(12) United States Patent
Jackson et al.

(10) Patent No.: US 11,724,110 B2
(45) Date of Patent: Aug. 15, 2023

(54) BRAIN STIMULATION THERAPY

(71) Applicant: Medtronic, Inc., Minneapolis, MN (US)

(72) Inventors: Jadin C. Jackson, Roseville, MN (US); Alan Shi, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/036,957

(22) Filed: Sep. 29, 2020

(65) Prior Publication Data

US 2022/0096842 A1   Mar. 31, 2022

(51) Int. Cl.
*A61N 1/05* (2006.01)
*A61N 1/36* (2006.01)

(52) U.S. Cl.
CPC ....... *A61N 1/36139* (2013.01); *A61N 1/0534* (2013.01); *A61N 1/36153* (2013.01); *A61N 1/36157* (2013.01); *A61N 1/36164* (2013.01)

(58) Field of Classification Search
CPC ............. A61N 1/36139; A61N 1/0534; A61N 1/36153; A61N 1/36157; A61N 1/36164
See application file for complete search history.

(56) References Cited

U.S. PATENT DOCUMENTS

| | | | |
|---|---|---|---|
| 8,359,100 B2 | 1/2013 | Cameron et al. | |
| 8,433,415 B2 | 4/2013 | Leiter et al. | |
| 8,892,206 B1 | 11/2014 | Swanson | |
| 9,603,522 B2 | 3/2017 | Lee et al. | |
| 9,872,757 B2 | 1/2018 | Kelly et al. | |
| 9,884,180 B1 | 2/2018 | Ho et al. | |
| 10,390,721 B2 | 8/2019 | Tcheng | |
| 10,441,791 B2 | 10/2019 | Bennet et al. | |
| 10,525,267 B2 | 1/2020 | Bouton et al. | |

(Continued)

FOREIGN PATENT DOCUMENTS

| | | |
|---|---|---|
| CN | 108310649 A | 7/2018 |
| CN | 110681050 A | 1/2020 |
| KR | 20150035345 A | 4/2015 |

OTHER PUBLICATIONS

Grahn et al., "A Neurochemical Closed-Loop Controller for Deep Brain Stimulation: Toward Individualized Smart Neuromodulation Therapies," Frontiers in Neuroscience, vol. 8, No. 169, Jun. 2014, 11 pp.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

A stimulation therapy system dynamically modifies therapy intensity based on measured neurotransmitter levels. In some examples, the system delivers, via an electrode implanted in a brain of a patient and stimulation circuitry, an electrical stimulus; monitors an electrical current generated by the stimulation circuitry to deliver the electrical stimulus; determines, based on the electrical current, a value representative of a concentration of dopamine in the brain of the patient; determines, based on the value representative of the concentration of dopamine, a value for one or more stimulation parameters that at least partially define electrical stimulation therapy; and delivers, via the electrode, the electrical stimulation therapy.

19 Claims, 7 Drawing Sheets

(56) References Cited

U.S. PATENT DOCUMENTS

| | | |
|---|---|---|
| 10,543,368 B2 | 1/2020 | Crowder et al. |
| 2006/0173509 A1 | 8/2006 | Lee et al. |
| 2006/0265024 A1* | 11/2006 | Goetz ................. A61N 1/3706 607/48 |
| 2009/0005833 A1 | 1/2009 | Cameron et al. |
| 2009/0216192 A1 | 8/2009 | Shriver et al. |
| 2012/0165634 A1* | 6/2012 | Lee ........................ A61B 5/00 600/345 |
| 2013/0123600 A1* | 5/2013 | Tcheng ................. A61B 5/291 600/378 |
| 2013/0289522 A1 | 10/2013 | Musallam et al. |
| 2014/0277279 A1* | 9/2014 | Cates .................. A61N 1/0556 607/59 |
| 2018/0272142 A1 | 9/2018 | Zhang et al. |
| 2019/0000332 A1 | 1/2019 | Li et al. |
| 2019/0151666 A1 | 5/2019 | Bonnet |
| 2019/0381325 A1 | 12/2019 | Regnier et al. |
| 2019/0388695 A1* | 12/2019 | Dinsmoor .............. G16H 20/30 |
| 2020/0108257 A1 | 4/2020 | Bouton et al. |
| 2021/0236821 A1* | 8/2021 | Sinclair .............. A61N 1/36139 |

OTHER PUBLICATIONS

Paek et al., "Dopamine Measurement During Prolonged Deep Brain Stimulation: a Proof-of Principle Study of Paired Pulse Voltammetry," Biomedical Engineering Letters, vol. 3, No. 1, Mar. 1, 2013, 16 pp.

Vajari et al., "Integrity Assessment of a Hybrid DBS Probe that Enables Neurotransmitter Detection Simultaneously to Electrical Stimualation and Recording," Micro Machines, vol. 9, No. 10, Oct. 2018, 15 pp.

Montague et al., "Computational Underpinnings of Neuromodulation in Humans," Cold Spring Harbor Symposia Quantitative Biology, Apr. 25, 2019, 19 pp.

International Search Report and Written Opinion of International Application No. PCT/US2021/050053, dated Jan. 4, 2022, 10 pp.

\* cited by examiner

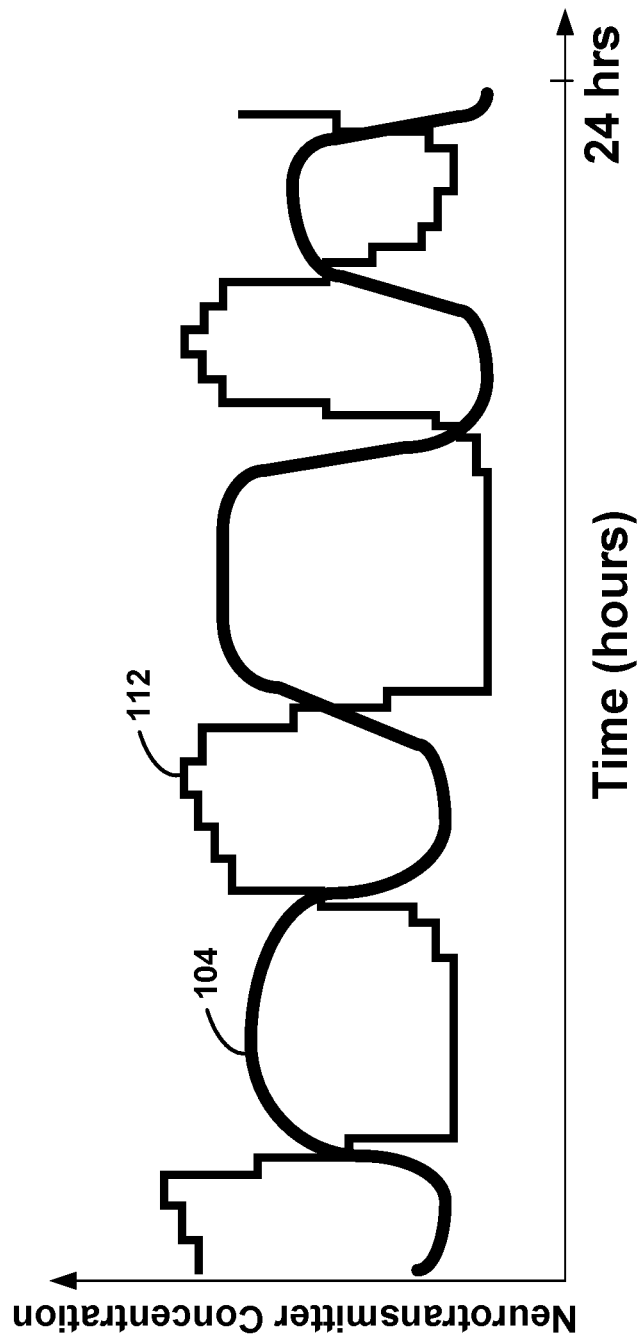

BRAIN STIMULATION THERAPY

TECHNICAL FIELD

The disclosure relates to brain stimulation therapy.

BACKGROUND

Implantable medical devices, such as electrical stimulators, may be used in different therapeutic applications, such as deep brain stimulation (DBS). A medical device may be used to deliver therapy to a patient to treat a variety of symptoms or patient conditions such as mood disorders, chronic pain, tremors, Alzheimer's disease, Parkinson's disease, other types of movement disorders, seizure disorders (e.g., epilepsy), or obesity. In some therapy systems, an external or implantable electrical stimulator delivers electrical therapy to a tissue site within a patient with the aid of one or more implanted electrodes, which may be deployed by medical leads or on a housing of the stimulator.

SUMMARY

In general, the disclosure is direct to methods and systems for delivering electrical stimulation to a brain of a patient. In accordance with some example techniques of this disclosure, stimulation therapy levels for electrical stimulation delivered to the brain of a patient may be selected based at least in part on patient neurotransmitter levels determined via cyclic voltammetry, e.g., as part of a closed-loop feedback technique in which neurotransmitter measurements are used to adjust one or more parameters of electrical stimulation therapy delivered to the patient. In some examples, electrical stimulation therapy pulses and cyclic voltammetry electrical signals may be delivered via one or more common electrodes, e.g., a common set or subset of electrodes, implanted within the brain of the patient. For example, an implantable medical device system may be configured such that the same electrode(s) are used to deliver electrical stimulus for the neurotransmitter measurements and to deliver the electrical stimulation therapy. In some examples, the cyclic voltammetry measurement electrical signals may be interleaved with, or partially or fully integrated within, the electrical stimulation therapy waveforms.

In this way, the one or more techniques of this disclosure may enable versatile selection of a subset of dual-function electrodes to sense neurotransmitter concentrations and/or deliver stimulation therapy from among a larger set of implanted electrodes, for example, to target precise locations within the patient's brain. For example, since the same electrodes can sense neurotransmitter concentrations and deliver stimulation, less surface area on a lead is taken up by electrodes that cannot provide stimulation therapy. Instead, every electrode can provide stimulation therapy which increases the programming flexibility and stimulation precision to desired tissue. Further, customizable, multiplexed sensing/stimming waveforms can provide virtually continuous, uninterrupted neurotransmitter monitoring and stimulation therapy delivery via a single integrated device.

In combination, these advantages enable monitoring of patient medication levels and/or adaptation of stimulation to medication levels; long-term monitoring of patient neurotransmitter levels (e.g., daily average levels); objective, instantaneous measurements of current medication absorption status by proxy of neurotransmitter levels; and intelligent, dynamic modifications of DBS-therapy settings in order to reduce patient symptoms and/or undesired side effects that may otherwise result from DBS therapy interacting with elevated neurotransmitter levels and/or medication levels.

In one example, the disclosure is directed to a method for delivering electrical stimulation, the method including: delivering, via an electrode implanted in a brain of a patient and stimulation circuitry, an electrical stimulus; monitoring an electrical current generated by the stimulation circuitry to deliver the electrical stimulus; determining, based on the electrical current, a value representative of a concentration of dopamine in the brain of the patient; determining, based on the value representative of the concentration of dopamine, a value for one or more stimulation parameters that at least partially define electrical stimulation therapy; and delivering, via the electrode, the electrical stimulation therapy.

In another example, the disclosure is directed to a system including an electrode configured to be implanted in a brain of a patient; stimulation circuitry; and processing circuitry configured to: cause the stimulation circuitry to deliver, via the electrode implanted in the brain of the patient, an electrical stimulus; monitor an electrical current generated by the stimulation circuitry to deliver the electrical stimulus; determine, based on the electrical current, a value representative of a concentration of dopamine in the brain of the patient; determine, based on the value representative of the concentration of dopamine, a value for one or more stimulation parameters that at least partially define electrical stimulation therapy; and cause the stimulation circuitry to deliver, via the electrode, the electrical stimulation therapy.

In another example, the disclosure is directed to a non-transitory, computer-readable medium comprising programming instructions that cause a processor to: deliver, via an electrode implanted in a brain of a patient and stimulation circuitry, an electrical stimulus; monitor an electrical current generated by the stimulation circuitry to deliver the electrical stimulus; determine, based on the electrical current, a value representative of a concentration of dopamine in the brain of the patient; determine, based on the value representative of the concentration of dopamine, a value for one or more stimulation parameters that at least partially define electrical stimulation therapy; and deliver, via the electrode, the electrical stimulation therapy.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 5A and 5B are graphs depicting examples of fluctuations in neurotransmitter levels in the brain of a patient over time.

DETAILED DESCRIPTION

Figure 1:
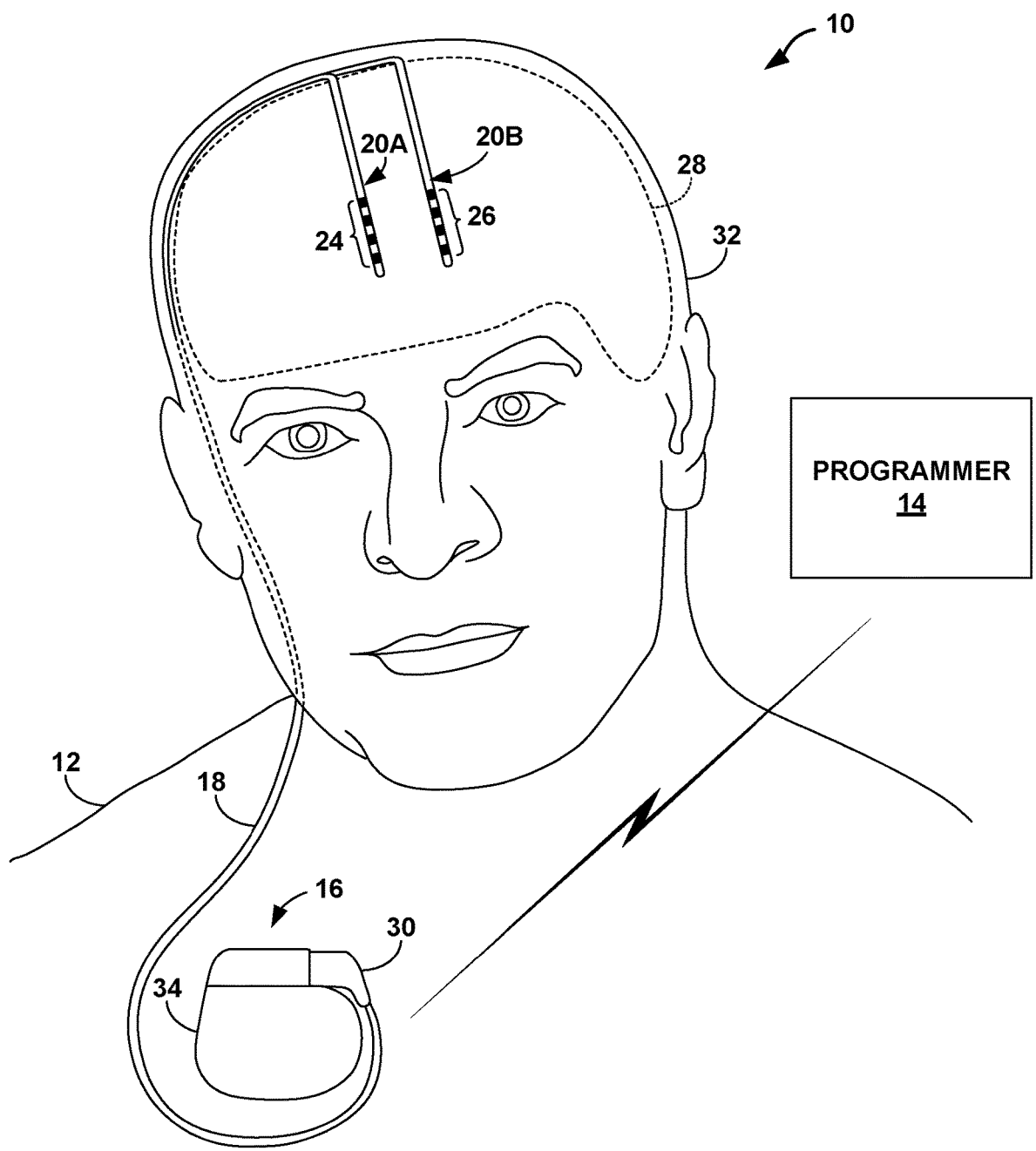
FIG. 1 is a conceptual diagram illustrating an example stimulation therapy system that is configured to deliver stimulation therapy to a patient.

In some examples of the present disclosure, deep-brain stimulation (DBS) may be delivered to a brain of a patient from a medical device to manage a patient disorder, such as a movement disorder (e.g., Parkinson's disease) or a mood disorder. In some cases, a patient may receive DBS treatment in addition to medication prescribed by a clinician to treat one or more symptoms of the patient disorder. However, in some such cases, DBS therapy may interact with high medication levels or medication states, resulting in undesired side effects. Accordingly, it may be critical to objectively measure and monitor indications of the patient medication state, since medication absorption may vary over time based on a plurality of factors such as, but not limited to, meal timing and content, and patient medication compliance (e.g., adherence to a prescribed consumption schedule). For example, cyclic voltammetry may be used to measure relative levels or concentrations of medication-induced neurotransmitter levels in the brain of the patient by delivering an electrical signal and then monitoring a resulting change in the electrical signal characteristic of the neurotransmitter levels. Some cyclic voltammetry systems include carbon-fiber electrodes to deliver these electrical signals, whereas DBS therapy systems more commonly include electrodes of other materials, such as platinum iridium (PlIr).

In accordance with the techniques of this disclosure, an integrated cyclic-voltammetry and DBS-therapy system is configured to deliver neurotransmitter-level-measurement electrical signals and DBS therapy electrical signals via a common set or subset of electrodes implanted within the brain of a patient, e.g., via at least one common electrode such that the electrode combinations share at least one electrode or the electrode combinations are the same. In some examples, a medical device includes DBS electrodes (e.g., platinum-iridium electrodes) positioned within a brain of a patient. Using the DBS electrodes, the medical device may deliver electrical signals used to conduct electrochemical measurements indicative of levels of one or more neurotransmitters in the brain of the patient, as well as deliver stimulation therapy at levels proportional to, or otherwise corresponding to, the measured neurotransmitter levels. In this way, some example techniques of this disclosure enable a continuous closed feedback loop of measuring neurotransmitter levels and providing a corresponding level of stimulation therapy via a common set or subset of DBS electrodes.

In some examples, a DBS system may be configured to deliver an electrical signal via a set of DBS electrodes to perform cyclic voltammetry to measure relative levels of one or more neurotransmitters, such as dopamine, serotonin, norepinephrine, or other neurotransmitters. Based on the measured levels of neurotransmitters, the DBS system may determine a corresponding level of intensity of stimulation therapy to treat a patient disorder. For example, the DBS system may determine a lower or reduced stimulation intensity in response to measuring elevated levels of neurotransmitters, or conversely, may determine a higher or increased stimulation intensity in response to measuring decreased levels of neurotransmitters. The DBS system may then deliver electrical stimulation therapy electrical signals via the same DBS electrodes or a common subset of DBS electrodes according to the determined corresponding therapy levels. The DBS system may perform subsequent cyclic voltammetry measurements to determine a change in the levels of neurotransmitters in the brain of the patient, and determine subsequent corresponding levels of stimulation therapy to deliver to the patient. For example, the DBS system may be configured to monitor dopamine or other neurotransmitter levels on a periodic or substantially continuous basis, and periodically or substantially continuously modify the intensity of delivered stimulation therapy based on the measured levels, so as to maintain a balanced, efficacious treatment of the patient condition as medication-induced and/or natural dopamine levels fluctuate within the brain of the patient over time.

By merging a cyclic voltammetry system and a DBS therapy system into a single device, the techniques of this disclosure provide for a number of benefits, such as, but not limited to, long-term monitoring of patient medication compliance and medication absorption; long-term monitoring of patient neurotransmitter levels (e.g., daily average levels); objective, instantaneous measurements of current medication absorption status by proxy of neurotransmitter levels; and intelligent, dynamic modifications of DBS-therapy settings in order to reduce patient symptoms and/or undesired side effects that may otherwise result from DBS therapy interacting with elevated neurotransmitter levels and/or medication levels.

Electrodes configured to both sense (e.g., measure) neurotransmitter levels via cyclic voltammetry as well as deliver stimulation therapy may enable significant precision in both techniques. For example, by using at least one common electrode for both functions, the techniques of this disclosure enable delivery of stimulation therapy to the precise location of the patient's brain where neurotransmitter levels were measured, ensuring a direct correlation between the measurement and the therapy. In another aspect, versatile electrodes configured to perform both functions significantly increases the permutations of electrodes that may be selected to perform either function, allowing for precise selection among the electrodes based on their implanted location, as compared to "dedicated" electrode combinations configured to perform just one function or the other. Further, by including a single set of versatile electrodes instead of two distinct sets of dedicated electrodes, the form factor of the integrated, dual-function device may be reduced for compactness and convenience. Put another way, sensing specific electrodes do not take up space on a lead that may otherwise be beneficial for an electrode to deliver electrical stimulation from that location.

Additionally or alternatively to integrating neurotransmitter measurement techniques and stimulation therapy techniques via a common set or subset of DBS electrodes, the techniques of this disclosure further include multiplexing (e.g., integrating, interleaving, and/or alternating between) electrical signals for neurotransmitter measurements and electrical signals for stimulation therapy into a common scheme or pattern (e.g., waveforms or pulses) of electrical signals. For example, a DBS system may "interleave," alternate between, or partially combine measurement signals and therapy signals, thereby enabling virtually continuous neurotransmitter monitoring and stimulation therapy delivery while maintaining discrete electrical pulse types uniquely tailored for each distinct function. In other examples in accordance with this disclosure, the DBS system may fully integrate the "sensing" electrical signals and the "stimming" electrical signals into a single, common electrical pulse type (e.g., shape) configured to perform both functions, thereby enabling simultaneous, uninterrupted neurotransmitter measurement and stimulation therapy delivery.

In some examples, the techniques of this disclosure include performing cyclic voltammetry measurements may by measuring currents of an electrical signal, evoked in response to an applied voltage delivered from one or more combinations of electrodes (e.g., electrode pairs), in order to determine neurotransmitter levels a target site, and then selecting, based on the measured currents, a set of electrode pairs to deliver therapeutic electrical stimulation.

Although described primarily with respect to brain applications involving neurotransmitter levels within the brain of a patient, the techniques of this disclosure may be highly adaptable to other patient applications, such as in the cardiac space, with regard to sensing blood hormone concentrations or related medications.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder (e.g., Parkinson's disease), a mood disorder, or other disorder of patient 12, e.g., by managing one or more symptoms of the disorder. Therapy system 10 may be used to manage the symptoms of patient 12 by reducing tremors, improving mood, facilitating memory recall, improving cognitive functioning, improving motor functioning, or reducing seizures, for example. The symptoms controlled by therapy system 10 may be dependent upon the diagnosis of patient 12, as well as the relative severity of symptoms. Patient 12 ordinarily will be a human patient. In some cases, however, therapy system 10 may be applied to other mammalian or non-mammalian non-human patients. While examples of the disclosure are described in some cases with regard to management of symptoms of a movement disorder, such as Parkinson's disease, in other examples, therapy system 10 may also deliver therapy to manage symptoms of other patient conditions, such as, but not limited to, mood disorders, Alzheimer's disease, seizure disorders such as epilepsy, psychological disorders, or other neurogenerative impairment.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep-brain stimulation (DBS) system because IMD 16 delivers electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28). In some examples, stimulation is delivered to the white matter tract of brain 28 to determine neural connectivity between a stimulation site and a target site in another region of brain 28. For example, during programming, stimulation may be delivered via a plurality of different electrode pairs or a combination of more than two electrodes, and the electrode combination providing the most-efficacious response may be determined based on evoked potentials. In some examples, therapeutic stimulation may be used to either deliver intermittent excitatory drive to a neural circuit, or to inhibit said circuit, based on the stimulation parameters. In other examples, consistent with this disclosure, therapy system 10 may deliver stimulation therapy to other target sites of a patient's body, such as a spinal cord, heart, and/or vagal nerve, as non-limiting examples.

Electrical stimulation generated from the stimulation generator 64 (FIG. 2) of IMD 16 may help prevent the onset of events associated with the patient's disorder or mitigate symptoms of the disorder. For example, electrical stimulation therapy delivered by IMD 16 to a stimulation site within brain 28 may reduce tremors, improve mood, facilitate memory recall, or improve cognitive function.

IMD 16 may deliver electrical stimulation therapy to brain 28 of patient 12 according to one or more stimulation therapy programs. A therapy program defines one or more electrical stimulation parameter values for therapy generated and delivered from IMD 16 to brain 28 of patient 12. In examples in which IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy program may include one or more electrode combinations, which can include selected electrodes (e.g., selected from electrodes 24, 26) and their respective polarities. The exact therapy parameter values of the stimulation therapy that helps prevent or mitigate symptoms, such as the amplitude or magnitude (electrical current or voltage) of the stimulation signals, the duration of each signal (e.g., in the case of stimulation pulses, a pulse width or duty cycle), the waveform of the stimuli (e.g., rectangular, sinusoidal or ramped signals), the frequency of the signals, cycling (whether stimulation is always on, or whether it is cycled on and off for predetermined periods of time) and the like, may be specific for the particular stimulation site (e.g., the area of the brain) involved as well as the particular patient and patient condition.

While stimulation pulses are primarily described herein, stimulation signals may be of any form, such as continuous-time signals (e.g., sine waves) or the like. As will be described further below, IMD 16 may be configured to modify one or more parameters of the electrical stimulation (e.g., by changing the value of one or more stimulation parameters) delivered to patient 12 based on a determined level of a neurotransmitter in brain 28 of patient 12.

In accordance with the techniques of this disclosure, in addition to delivering stimulation therapy to manage a symptom of patient 12, therapy system 10 is configured to monitor relative concentrations or levels of one or more chemical neurotransmitters (e.g., dopamine, serotonin, norepinephrine, etc.) within brain 28 of patient 12. For example, IMD 16 may include a sensing module 66 (FIG. 2) that senses neurotransmitter levels within one or more regions of brain 28. The neurotransmitter levels at one or more locations within brain 28 of patient 12 may vary over time rather than remain constant.

As one example, IMD 16, using sensing module 66, may be configured to perform cyclic voltammetry via electrodes 24, 26 to measure neurotransmitter levels within brain 28 of patient 12. As used herein, "cyclic voltammetry" may refer to a potentiodynamic electrochemical measurement in which the voltage across a reference electrode (e.g., either of electrodes 24, 26) is increased from a first voltage to a second voltage and then reduced back to the first voltage. While the voltage is increased and decreased, a corresponding electrical current is measured at the reference electrode. A plot or graph of the measured current as a function of the applied voltage is referred to as a "cyclic voltammogram trace," and unique properties (e.g., dimensions) of the trace may be used to infer levels of neurotransmitters or other neurochemicals that factored into (e.g., resulted in) the measured current. In the present example, sensing module 66 may be configured to control a voltage across stimulation electrodes 24, 26, and measure the corresponding electrical current at one of the electrodes.

In accordance with the techniques of this disclosure, IMD 16 is configured to control (e.g., capable of controlling) the voltage across the same set, or a common subset, of electrodes 24, 26, for both cyclic-voltammetry measurements and for stimulation therapy delivery. In other words, the "sensing" (e.g., neurotransmitter measurement) electrode combination and the "stimulation" electrode combination share at least one common electrode (e.g., the common subset of electrodes) between them. In this manner, the electrode combination that includes electrodes for performing cyclic-voltammetry measurements may share a common electrode, but still be different than, the electrode combination selected to deliver stimulation therapy. In other examples, the electrode combination used to perform cyclic-voltammetry measurements may be exactly the same (e.g., include only the same electrodes) as the electrode combination selected to deliver stimulation therapy. As one illustrative example, IMD 16 may control a voltage between electrodes 24A and 26A of FIG. 1 while performing cyclic voltammetry, and control a voltage between electrodes 24A and 26A to deliver stimulation therapy (e.g., all electrodes shared in common). As another example, IMD 16 may control a voltage between electrodes 24A and 26A while performing cyclic voltammetry, and control a voltage between electrodes 24A and 26B to deliver stimulation therapy (e.g., only one electrode shared in common). In other examples, the sensing electrodes and the stimulation electrodes may not share a common electrode. For example, although all of the electrodes 24, 26 may be of a common electrode type (e.g., platinum-iridium electrodes) that are capable of performing both neurotransmitter sensing and providing stimulation therapy, in some cases, IMD 16 may select two distinct subsets of electrodes from electrodes 24, 26 for performing each function, as described further below.

As detailed further with respect to FIGS. 4A-4E, below, IMD 16 may further be configured to perform cyclic voltammetry measurements via one or more of electrodes 24, 26, by alternating measurement signals with stimulation therapy signals, by interleaving measurement signals with therapy signals, or by partially or fully integrating measurement signals and therapy signals.

In some examples, the sensing module 66 of IMD 16 may receive the cyclic voltammetry measurements from electrodes 24, 26 or other electrodes positioned to monitored neurotransmitters or other brain signals of patient 12. In the example shown in FIG. 1, the signals generated by electrodes 24, 26 are conducted to the sensing module within IMD 16 via conductors within the respective lead 20A, 20B. Electrodes 24, 26 may also be used to deliver electrical stimulation from the therapy module to stimulation sites within brain 28 as well as sense neurotransmitter levels (e.g., via cyclic voltammetry) within brain 28. For example, electrodes 24, 26, may include standard stimulation electrodes, e.g., electrodes composed of a platinum-iridium ("PtIr") alloy.

In some examples, the sensing module of IMD 16 may sense neurotransmitter levels via one or more of the electrodes 24, 26 that are also used to deliver electrical stimulation to brain 28. In some examples, the sensed cyclic voltammetry measurements (e.g., indicative of neurotransmitter levels) may be collected near the target stimulation site. For example, as described herein, IMD 16 enables "local" cyclic voltammetry measurements of neurotransmitter levels within the same area or region of the brain 28 where IMD 16 delivers stimulation therapy, for example, to target precise locations within the patient's brain, thereby providing a strong correlation between neurotransmitter measurements and the stimulation therapy delivered in response to the measurements.

In other examples, one or more of electrodes 24, 26 may be used to sense neurotransmitter levels and/or bioelectrical brain signals while one or more different electrodes 24, 26 may be used to deliver electrical stimulation. In some examples, the stimulation site for stimulation and the sensing site may be different, such as different hemispheres of brain 28. The sensing site may be the same or different from the target stimulation site. For example, although dopamine and norepinephrine neurons are generally considered to be relatively non-selective (e.g., broad) with regard to the areas into which they release their neurotransmitters, sensing from a different region or hemisphere of the brain than where stimulation therapy is delivered may also be of interest.

Depending on the particular stimulation electrodes and sense electrodes used by IMD 16, IMD 16 may monitor neurotransmitter levels and deliver electrical stimulation at the same region of brain 28 or at different regions of brain 28. In some examples, the electrodes used to sense neurotransmitter levels may be located on the same lead used to deliver electrical stimulation, while in other examples, the electrodes used to sense neurotransmitter levels may be located on a different lead than the electrodes used to deliver electrical stimulation. In some examples, the sensing module that senses neurotransmitter levels of brain 28 (e.g., the sensing module that measures an electrical signal indicative of a level of a neurotransmitter present within brain 28) is in a physically separate housing from outer housing 34 of IMD 16. However, in the example shown in FIG. 1 and the examples primarily referred to herein for ease of description, the sensing module and therapy module of IMD 16 are enclosed within a common outer housing 34.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 is constructed of a biocompatible material that resists corrosion and degradation from bodily fluids. IMD 16 can comprise a hermetic outer housing 34, which substantially encloses components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. In other examples, leads 20 may include just a single lead, or in other examples, more than two leads. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a condition of patient 12. Leads 20 may be implanted to position electrodes 24, 26 at a target implantation site within brain 28 via any suitable technique, such as through respective burr holes in a skull of patient 12 or through a common burr hole in the cranium 32. Leads 20 may be placed at any location within brain 28 such that electrodes 24, 26 are capable of providing electrical stimulation to one or more stimulation sites within brain 28 during treatment.

Different neurological or psychiatric disorders may be associated with activity in one or more of regions of brain 28, which may differ between patients. For example, in the case of Parkinson's disease, a mood disorder, seizure disorder, or Alzheimer's disease, leads 20 may be implanted to deliver electrical stimulation to regions within the Circuit of Papez, such as, e.g., the anterior nucleus (AN), the internal capsule, the cingulate, the fornix, the mammillary bodies, the mammillothalamic tract (mammillothalamic fasciculus), and/or hippocampus (HC). Regions of brain 28 may be functionally connected to one another via neurological and/or neurochemical pathways such that activity or stimulation delivered within one region of brain 28 may affect activity within another region of brain 28. In some examples, neurotransmitter levels can be indicated by a signal characteristic (e.g., an amplitude, frequency, and/or frequency domain characteristic) of a measured electrical current corresponding to a voltage applied across one of electrodes 24, 26. In some examples, but not all examples, the signal characteristic of a neurotransmitter level sensed within a particular region of brain 28 may change as an applied stimulation therapy in the region changes.

IMD 16 may deliver therapy to the brain 28 in a manner that influences one or more symptoms of a patient disorder. For example, IMD 16 may deliver therapy to the fornix, or other suitable region of brain 28 to control a brain state of patient 12 (e.g., as indicated by cyclic voltammetry measurements of neurotransmitters such as dopamine or serotonin) in a manner that effectively treats a disorder or symptom of patient 12. For example, in the case of a movement disorder, such as Parkinson's disease, IMD 16 may deliver therapy to a region of brain 28 via a selected subset of electrodes 24, 26 (e.g., the stimulation electrode combination) to reduce tremors of patient 12.

In some examples with this disclosure, a patient may take medication to treat a patient disorder, e.g., to modify a patient condition from a condition associated with an undesirable baseline brain state (e.g., a baseline brain state exhibited by patient 12 in the absence of therapy or medication) to characteristics associated with a desirable brain state. For example, in a desirable brain state, the neurotransmitter levels (e.g., as determined via the sensing module of IMD 16) may be indicative of a patient state in which the patient condition is treated, e.g., wherein one or more symptoms of the patient disorder are mitigated or even eliminated. For example, in the case of a movement disorder such as Parkinson's disease, patient 12 may take medication configured to maintain neurotransmitter levels within a predetermined desirable range of neurotransmitter levels. While neurotransmitter levels remain within this range, the patient may experience reduced or eliminated tremors, as one example. If neurotransmitter levels fall below the desirable range, patient symptoms, such as tremors, may reappear.

In some examples, additionally or alternatively to consuming medication, patient 12 may receive DBS therapy to address the same or different symptoms of the patient disorder. For example, activation of a region of the patient's brain may reduce patient tremors, elevate a patient mood, enable better cognitive function of the patient, or aid in memory recall tasks. However, in some cases, the combination of elevated neurotransmitter levels caused by medication and higher levels of stimulation therapy may result in undesirable side effects to patient 12. Accordingly, DBS system 10 is configured to measure relative levels or concentrations (or change in levels) of one or more neurotransmitters, and then determine, based on the measured relative levels, a corresponding level of stimulation therapy, e.g., that is appropriate for delivery in view of the measured neurotransmitter levels, to deliver to patient 12. As an illustrative example, DBS system 10 may measure, via cyclic voltammetry, relatively higher concentrations of dopamine within the brain of patient 12, and control the delivery of electrical stimulation, based on the higher dopamine levels, that has a relatively low stimulation intensity. Conversely, DB S system 10 may measure, via cyclic voltammetry, relatively lower concentrations of dopamine within the brain of patient 12, and control the delivery of electrical stimulation, based on the lower dopamine levels, that has a relatively high stimulation intensity.

Upon delivering stimulation therapy to address a patient condition or symptom, IMD 16 may be configured to perform subsequent measurements, e.g., via cyclic voltammetry, to identify subsequent levels of neurotransmitters and/or the changes in neurotransmitter levels, as the neurotransmitter levels fluctuate over time due to, for example, an amount of time elapsed since the patient consumed medication, patient medication compliance, and/or an amount and content of consumed food as well as duration since the food was consumed, among other variables. The subsequent measurements may then be used to inform or determine a subsequent level of stimulation therapy, as part of a closed feedback loop of neurotransmitter-level measurements and delivery of corresponding levels of stimulation therapy.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In some examples, stimulation therapy electrodes 24, 26 may include platinum electrodes, or electrodes including or otherwise formed of a platinum-iridium alloy. In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In some examples, electrodes 24, 26 may include one or more full ring electrodes in combination with one or more segmented electrodes. An example would be a "1-3-3-1" lead having a distal ring electrode; two rows each having three segmented electrodes, and a more proximal ring electrode. Such a lead is described in U.S. Pat. No. 7,668,601 assigned to the assignee of the current application. In still other examples, the complex electrode array may comprise electrodes formed using thin film techniques and the array may comprise any number of electrodes, such as forty or more electrodes. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In some such examples, IMD 16 may conduct neurotransmitter measurements and/or stimulation therapy delivery between at least one electrode 24, 26 embedded within the brain of patient 12, and the housing 34 of IMB 16. In some such examples, the larger surface area resulting from either or both of the housing 34 as compared to a smaller electrode 24, 26, and/or the larger amount of patient tissue between the brain implant site and the IMB implant site (e.g., the upper chest) may correspond to a lower current density from the electrical measurement signals and/or the electrical therapy signals, thereby potentially reducing possible adverse side effects from stimulation a large volume of tissue. Such systems may be referred to as "monopolar" in reference to the use of only one electrode 24, 26 used on leads 20 at a time. By contrast, systems configured to provide an electrical signal between at least two electrodes 24, 26 in which both electrodes are coupled to leads 20 may be referred to as "bipolar." The techniques of this disclosure may enable both monopolar and bipolar functions, according to the unique needs of each patient.

In other examples, one or both leads 20 may have a shape other than elongated cylinders as shown in FIG. 1. For example, leads 20 may be paddle leads, spherical leads, bendable leads, or any other type of shape effective in treating patient 12.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. For example, the display may be configured to output an indication of neurotransmitter levels or concentrations in response to cyclic voltammetry measurements.

In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function, e.g., a power button, or the buttons and the keypad may be soft keys that change in function depending upon the section of the user interface currently viewed by the user. In some examples, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, information on patient anatomy (e.g., imaging data such as CT or MM data) and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may deliver efficacious therapy to patient 12 to address symptoms associated with the movement disorder, mood disorder, or other patient condition. During the programming session, patient 12 may provide feedback to the clinician as to the efficacy of the specific program being evaluated or the clinician may evaluate the efficacy based on one or more physiological parameters of patient (e.g., heart rate, respiratory rate, or muscle activity).

Programmer 14 may also be configured for use by patient 12 in some examples. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Whether programmer 14 is configured for clinician or patient use, programmer 14 is configured to communicate to IMD 16 and, optionally, another computing device, via wireless communication. Programmer 14, for example, may be configured to communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may deliver stimulation on a periodic basis, or on demand. In some examples, programmer 14 may be a patient programmer whereby a patient may initiate the delivery of stimulation. For example, patient 12 may provide input initiating excitatory stimulation in order to reduce tremors or improve mood, cognitive function, or memory. In other examples, patient 12 may provide input indicating the effect desired, and programmer 14 will select between a plurality of programs based on the desired effect. The desired effect may be, for example, either excitatory or inhibitory stimulation. In some examples, stimulation therapy may be delivered in response to measuring, via cyclic voltammetry, a corresponding level of a particular neurotransmitter. In some examples, stimulation may be delivered at predetermined times of the day. The predetermined times of day may align with certain behaviors of patient 12. For example, waking or sleeping.

Therapy system 10 may be implemented to deliver chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 delivers effective treatment to patient 12, the clinician may implant a chronic stimulator within patient 12 for relatively long-term treatment.

Figure 2:
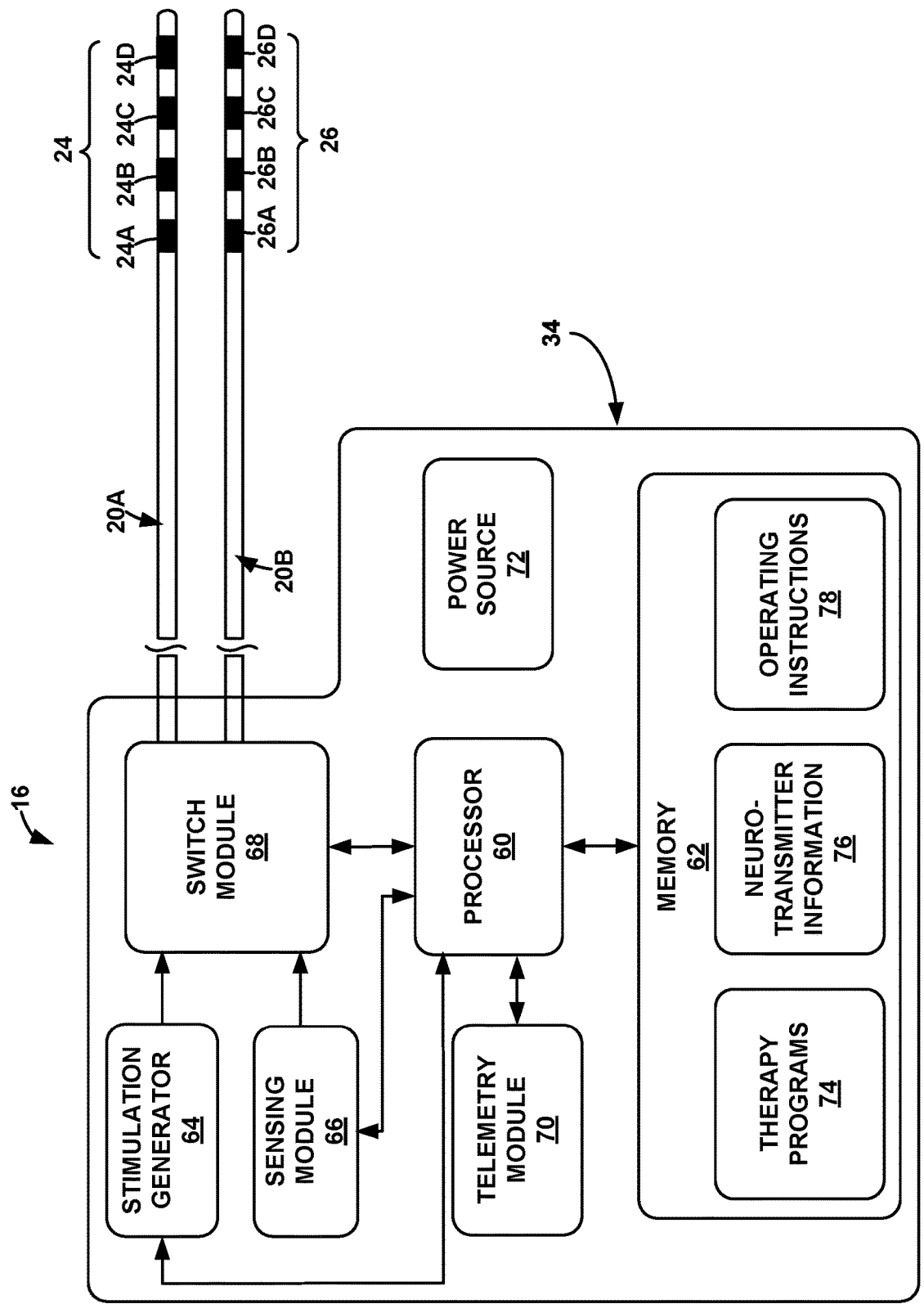
FIG. 2 is a functional block diagram illustrating example components of the implantable medical device of FIG. 1.

FIG. 2 is a functional block diagram illustrating components of IMD 16. In the example shown in FIG. 2, IMD 16 includes processor 60, memory 62, stimulation generator 64, sensing module 66, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74, neurotransmitter information 76, and operating instructions 78 in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal (FIGS. 4A-4E). In examples when IMD 16 delivers electrical stimulation therapy on a cyclic basis (as compared to on-demand), memory 62 stores, e.g., as part of therapy programs 74, cycle parameter information, such as, on-cycle time duration and off-cycle time duration. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Neurotransmitter information 76 stored by memory 62 can include neurotransmitter levels measured within one or more regions of brain 28 according to cyclic voltammetry measurements from sensing module 66. Neurotransmitter information 76 may include a type of neurotransmitter (e.g., dopamine, serotonin, etc.), a time of the measurement, and/or a location of the measurement within brain 28.

In some examples, processor 60 may determine a neurotransmitter level within a particular region of brain 28 of patient 12 based on cyclic voltammetry measurements performed by sensing module 66 via a subset of electrodes 24, 26, which may be referred to herein as a "sense" or "sensing" electrode combination. Thus, in some examples, processor 60 stores sensed neurotransmitter levels as neurotransmitter information 76. Operating instructions 78 guide general operation of IMD 16 under control of processor 60, and may include instructions for monitoring neurotransmitter levels within one or more brain regions via electrodes 24, 26 and/or selecting one or more stimulation therapy parameters based on the measured neurotransmitter levels. Operating instructions 78 may also include instructions for selecting one or more therapy parameters based on input from a user.

Stimulation generator 64, under the control of processor 60, generates stimulation signals for delivery to patient 12 via selected combinations of electrodes 24, 26. In some examples, during therapy delivery (versus performing cyclic voltammetry measurements) to manage a patient symptom, stimulation generator 64 generates and delivers stimulation signals to one or more target regions of brain 28 (FIG. 1), e.g., the fornix, of patient 12 via a selected combination of electrodes 24, 26 (referred to herein as a "stimulation," "stim" or "stimming" electrode combination) where the stimulation signals have a frequency in a range of about 30 Hertz (Hz) to about 150 Hz, a voltage of about 0.1 volts to about 10.5 volts, and a pulse width of about 60 microseconds to about 450 microseconds. In some examples, the stimulation signals have a frequency of 40 Hz, a voltage of about 3 volts, and a pulse width of about 150 microseconds. In addition, in some examples, the stimulation signals have a frequency of 40 Hz, a voltage of about 6 volts, and a pulse width of about 150 microseconds.

In some examples, the stimulation signals have a frequency of approximately 5 Hz. Stimulation may be delivered at a constant frequency, with the amplitude of the stimulation slowly changing over time. For example, stimulation may be delivered starting at approximately 1.5 V and be incrementally increased to approximately 8 V, e.g., in intervals of 0.5 V. Other stimulation parameter values and other therapy cycles are contemplated. Other ranges of therapy parameter values may also be useful, and may depend on the stimulation site within patient 12, which may or may not be within brain 28.

Processor 60, alone or in combination with sensing module 66, is configured to determine (e.g., estimate) relative concentrations (e.g., levels) of one or more neurotransmitters based on cyclic voltammetry measurements. For example, processor 60 may be configured to detect oscillation in the measured neurotransmitter level over time. Processor 60 may determine the length of time the oscillation in the amplitude of the sensed neurotransmitter level is present, as well as the frequency of the oscillation.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof. Processor 60 is configured to control stimulation generator 64 according to therapy programs 74 stored in memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across the electrodes 24, 26 of the selected stimulation electrode combination.

Switch module 68 may be a switch array, switch matrix, multiplexer, or any other type of switching module configured to selectively couple stimulation energy to selected electrodes 24, 26 and to selectively perform cyclic voltammetry with selected electrodes 24, 26 to measure neurotransmitter levels. Hence, stimulation generator 64 is coupled to electrodes 24, 26 via switch module 68 and conductors within leads 20. In some examples, however, IMD 16 does not include switch module 68. For example, in some examples each electrode is connected to a dedicated controllable current source and current sink.

Stimulation generator 64 may be a single channel or multi-channel stimulation generator. In particular, stimulation generator 64 may be capable of delivering, a single stimulation pulse, multiple stimulation pulses, or a continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time-divide the output of stimulation generator 64 across different stimulation electrode combinations at different times to deliver multiple programs or channels of stimulation energy to patient 12.

Sensing module 66 is configured to measure neurotransmitter levels of patient 12 via a sense electrode combination, which can include a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively measure neurotransmitter levels with different combinations of electrodes 24, 26 (and/or a reference other than an electrode 24, 26). As previously described, processor 60 may monitor the brain state of patient 12 via the measured neurotransmitter levels. In examples without a switch module 68, processor 60 may select each electrode individually. Although sensing module 66 is incorporated into a common outer housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 is configured to deliver operating power to various components of IMD 16. Power source 72 may include, for example, a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
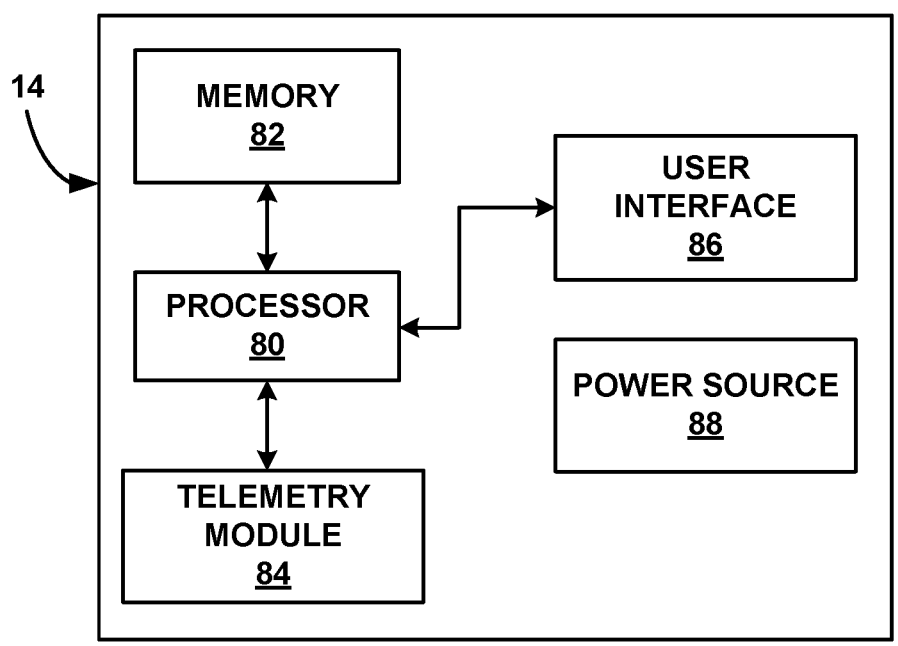
FIG. 3 is a functional block diagram illustrating example components of the medical device programmer of FIG. 1.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as an LCD, LED display, or other type of screen configured to present information related to the therapy, such as information related to neurotransmitter levels measured via one or more of a plurality of sense electrode combinations in response to the delivery of stimulation to brain 28. In addition, user interface 86 may include an input mechanism to receive input from the user. The input mechanisms may include, for example, buttons, a keypad (e.g., an alphanumeric keypad), a peripheral pointing device or another input mechanism that allows the user to navigate through user interfaces presented by processor 80 of programmer 14 and provide input.

As discussed above, if programmer 14 includes buttons and a keypad, the buttons may be dedicated to performing a certain function, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, dedicated keys within user interface 86 may be associated with a particular symptom (e.g., tremors resulting from an undesirable or below-threshold neurotransmitter level). Patient 12 may initiate the delivery of stimulation to alleviate a symptom (e.g., tremors) simply by pressing the key associated with the particular symptom. In some examples, processor 80 may limit the number of times stimulation may be delivered within a certain time frame in response to patient input.

In some examples, at least some of the control of stimulation delivery by IMD 16 may be implemented by processor 80 of programmer 14. For example, in some examples, processor 80 may control stimulation generator 64 of IMD 16 to generate and deliver electrical stimulation to a plurality of areas of brain 28 and may further control sensing module 66 to sense a neurotransmitter level within brain 28.

Memory 82 may include instructions for operating user interface 86 and telemetry module 84, and for managing power source 88. Memory 82 may also store any therapy data retrieved from IMD 16, such as, but not limited to, therapy parameters and time of delivery of therapy. The clinician may use this therapy data to determine the progression of the patient condition in order to plan future treatment for the disorder (or patient symptoms) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium-ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

FIGS. 4A-4E depict five example electrical waveforms 90A-90E, respectively, in accordance with techniques of this disclosure. As described above, therapy system 10 includes a plurality of electrodes 24, 26 configured to deliver stimulation therapy electrical signals (e.g., pulses 92) in order to manage one or more symptoms of a patient condition. Electrodes 24, 26 are further configured to deliver electrical signal 94 in order to perform cyclic voltammetry to determine and monitor neurotransmitter levels, which may fluctuate naturally over time and/or in response to medication consumed by the patient. In some cases, but not all cases, the patient medication is prescribed to manage one or more of the same symptoms as the DBS therapy stimulus 92. As defined and used herein, therapy signals or pulses 92 include any segment of an electrical waveform intended and configured to provide stimulation therapy to a patient, whereas measurement signals or pulses 94 include any segment of an electrical waveform during which sensing module 66 (FIG. 2) monitors a change in electrical current for the purpose of determining neurotransmitter levels.

In accordance with the techniques of this disclosure, therapy system 10 is configured to generate and deliver, via one or more of electrodes 24, 26, one or more pre-defined, multiplexed waveforms 90A-90E configured to both enable cyclic voltammetry measurements of neurotransmitter levels and deliver stimulation therapy, e.g., at levels corresponding to (e.g., inversely proportional to) the measured neurotransmitter levels. As used herein, a stimulation therapy "level" refers to the relative intensity of the stimulation therapy, which may be a function of one or more variable (e.g., modifiable) therapy parameters such as, but not limited to, an electrical pulse width or shape, an electrical current amplitude, a voltage amplitude, a pulse frequency, and/or a particular electrode combination (e.g., a location of electrodes that are activated). In the case of stimulation patterns, relevant therapy parameters might include burst frequency, burst duration, inter-burst interval, or rate of interleaving if multiple electrodes are being used. For more complex or stochastic patterns, other modifiable therapy parameters may include center frequency, average rate, average amplitude, or other similar parameters.

At a circuit-level implementation, therapy system 10 (e.g., switch module 68 of FIG. 2) may generate and deliver one or more multiplexed waveforms by switching between stimulation circuitry 64 and impedance-measurement circuitry, such as when electrical current waveforms can be sensed during a voltage sweep. In some examples, therapy system 10 is configured to sense the electrical current waveform throughout the stimulation waveform 92 and use that to compute a re-dox associated with a specific neurotransmitter concentration. For example, therapy system 10 may be configured to conserve power by activating ultra-sensitive current-sensing circuitry only during relatively infrequent voltage ramps intended for cyclic voltammetry. In such cases, switch module 68 may be configured to multiplex between the therapeutic stimulation circuity 64 and specialized sensing circuitry 66.

Waveforms 90A-90E are merely exemplary of such waveforms configured to perform these dual measurement-and-therapy functions, and are not intended to be limiting. In some examples, IMD 16 is configured to deliver therapy pulses 92 and measurement pulses 94 via the same electrode combination (or electrode combinations that have a common subset of one or more electrodes) of electrodes 24, 26. In other examples, IMD 16 may include some combinations of electrodes 24, 26, to deliver therapy pulses 92 and other combinations of electrodes 24, 26, to deliver measurement pulses 94.

Waveforms 90A-90E may include any suitable wavelength and frequency (e.g., duration). For example, IMD 16 may include a higher frequency of measurement pulses 94, and/or a larger measurement-pulse-to-stimulation-pulse ratio to sense neurotransmitter levels, during a period leading up to a dopamine release, for example, in response to consumed medication, in order to more-precisely determine corresponding stimulation therapy levels.

Figure 4A:
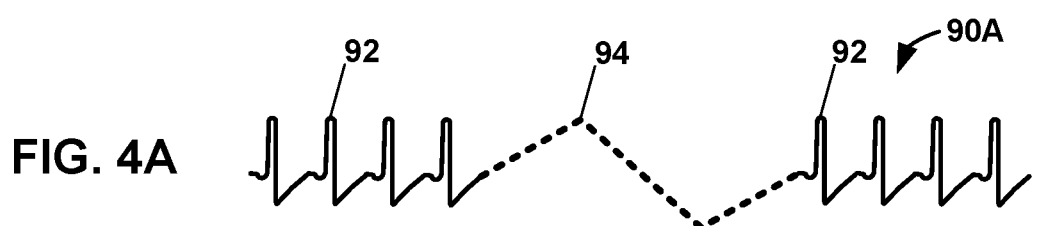
FIGS. 4A-4E are conceptual diagrams depicting five example electrical waveforms.

FIG. 4A depicts a first example waveform 90A. Waveform 90A includes stimulation therapy pulses 92 "interleaved" with cyclic voltammetry measurement pulses 94. The example waveform 90A includes relatively longer, uninterrupted periods of therapy pulses 92 interleaved with similarly relatively longer, uninterrupted periods of measurement pulses 94. These respective time periods may include virtually any duration, such as 1 second, 1 minute, or 1 hour. Although not explicitly shown in FIG. 4A, waveform 90A may be used for therapy programs including "cycled therapies," in which therapy levels (e.g., maximum amplitudes of the voltages of consecutive therapy pulses) are varied over time. Although waveform 90A depicts an alternating arrangement of four therapy pulses 92 and one measurement pulse 94, waveform 90A may include any ratio of therapy pulses 92 to measurement pulses 94; FIG. 4A is illustrates an example concept of interleaved periods of relatively longer, uninterrupted patterns of each type of electrical pulse 92, 94.

Figure 4B:
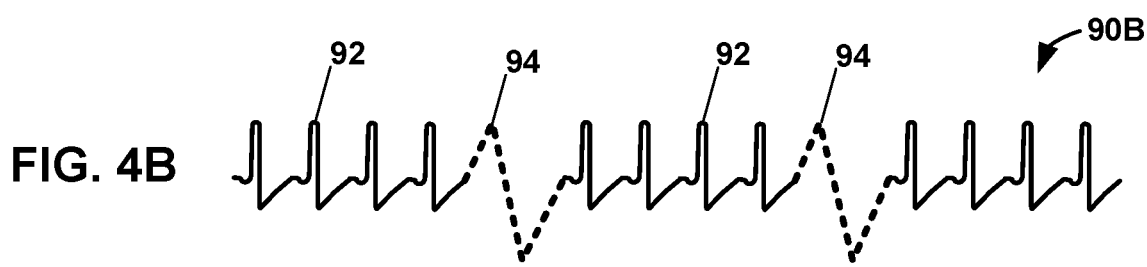

FIG. 4B depicts a second example waveform 90B. Waveform 90B includes stimulation therapy pulses 92 "integrated" (e.g., partially integrated) with cyclic voltammetry measurement pulses 94. The example waveform 90B includes instances of one or more measurement pulses 94 integrated with relatively shorter periods of therapy pulses 92. Although waveform 90B depicts an alternating arrangement of four therapy pulses 92 and one measurement pulse 94, waveform 90B may include virtually any ratio of therapy pulses 92 to measurement pulses 94; FIG. 4B illustrates an example concept of relatively more-frequent alternations between therapy pulses 92 and measurement pulses 94. These time periods may occur on relatively smaller timescales, such as on the order of tens of milliseconds to hundreds of milliseconds.

Figure 4C:
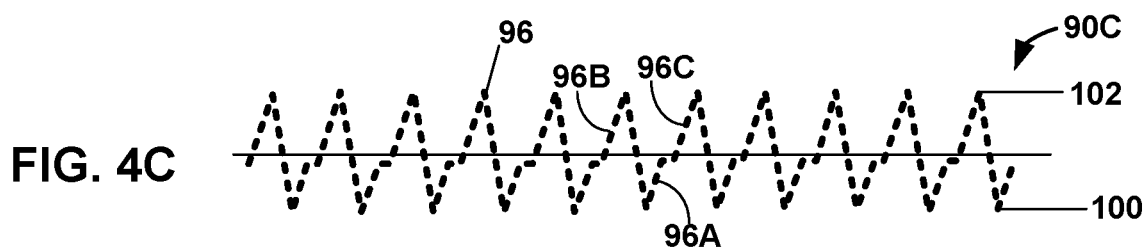

FIG. 4C depicts a third example waveform 90C. Waveform 90C includes stimulation therapy pulses 92 fully integrated (e.g., merged) with cyclic voltammetry measurement pulses 94, resulting in a series of combined pulses 96 configured to simultaneously deliver stimulation therapy and conduct cyclic voltammetry measurements. In the example shown in FIG. 4C, each combined electrical pulse 96 having a pulse shape that includes or approximates a triangle wave, or a biphasic V-shaped pulse, whereby therapy system 10 increases a pulse voltage (e.g., using a continuous rate ramp) of the common pulse 96 from a minimum voltage 100, up to a therapy-level voltage 102 while monitoring the resulting electrical current, and then reduces the pulse voltage from the therapy-level voltage 102 back to the minimum voltage 100. In some examples, a cyclic voltammetry measurement requires a sweep across a voltage range between a minimum voltage 100 of about −0.6 Volts to about −0.4 Volts, and a maximum voltage 102 of about 1.0 Volts to about 1.4 Volts. In some examples, therapy system 10 may perform each cyclic voltammetry measurement using the minimum-voltage-to-zero-voltage portion 96A at the end of one pulse 96, and either the zero-voltage-to-maximum-voltage portion 96B of the same pulse, or the zero-voltage-to-maximum-voltage portion 96C of the next consecutive pulse. As shown in FIG. 4C, pulses 96 of waveform 90C may each include an asymmetric triangle wave, at least partially incorporating the asymmetric features of therapy pulses 92.

Figure 4D:
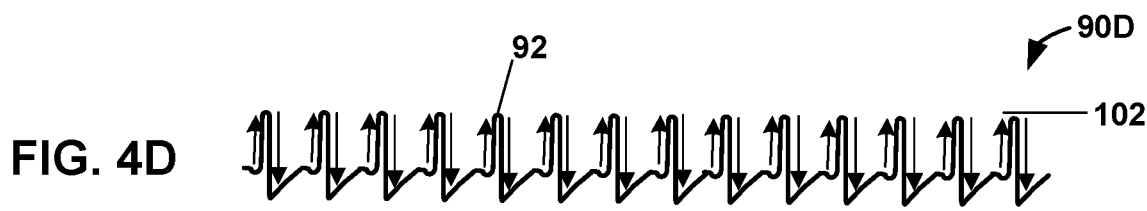

FIG. 4D depicts a fourth example waveform 90D. Waveform 90D includes a continuous pattern consisting of only stimulation therapy pulses 92 and no designated measurement pulses 94. That is, measurement pulses 94 have been replaced by therapy pulses 92, such that therapy system 10 is configured to perform cyclic voltammetry measurements using the therapy pulses 92. More specifically, as indicated by the directional arrows in FIG. 4D, therapy system 10 is configured to measure an induced current while the voltage increases up to a therapy-level voltage 102 and then again as the voltage is decreased back down from the therapy-level voltage 102.

Figure 4E:
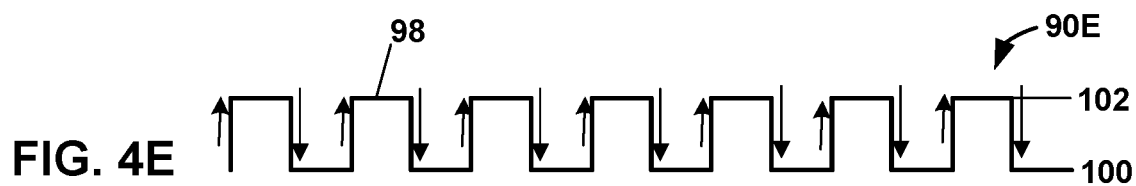

FIG. 4E depicts a fifth example waveform 90E. Waveform 90E includes no distinct stimulation therapy pulses 92 nor distinct measurement pulses 94, but instead, includes a continuous pattern of pulses 98 configured to simultaneously deliver stimulation therapy and conduct cyclic voltammetry measurements. In the example shown in FIG. 4E, each electrical pulse 98 having a pulse shape that includes or approximates a square wave (e.g., a rectangular-shaped wave), whereby therapy system 10 increases a pulse voltage of the common pulse 98 from a minimum voltage 100, up to a therapy-level voltage 102 while monitoring the resulting electrical current, and then reduces the pulse voltage from the therapy-level voltage 102 back to the minimum voltage 100.

In any of waveforms 90C-90E, IMD 16 may be configured to only record or measure the induced electrical current during an initial phase of each pulse, in which the electrical current is indicative of neurotransmitter concentration according to techniques of cyclic voltammetry. In any of the above waveforms 90A-90E, any depicted decrease in electrical voltage may indicate a passive charge-balancing phase (e.g., passive recharge). For example, FIGS. 4A and 4B depict waveforms including distinct charge-balancing phases. Waveforms 90C-90E of FIGS. 4C-4E, respectively, may include a charge-balancing phase as an active portion of each electrical pulse, wherein oxidation-reduction phases are part of the cyclic voltammetry measurements and are configured to be charge-balanced. Such waveforms may enable conservation of limited electrical power resources (e.g., battery capacity) as compared to systems that include active voltage ramping in both positive and negative directions.

Figure 5A:
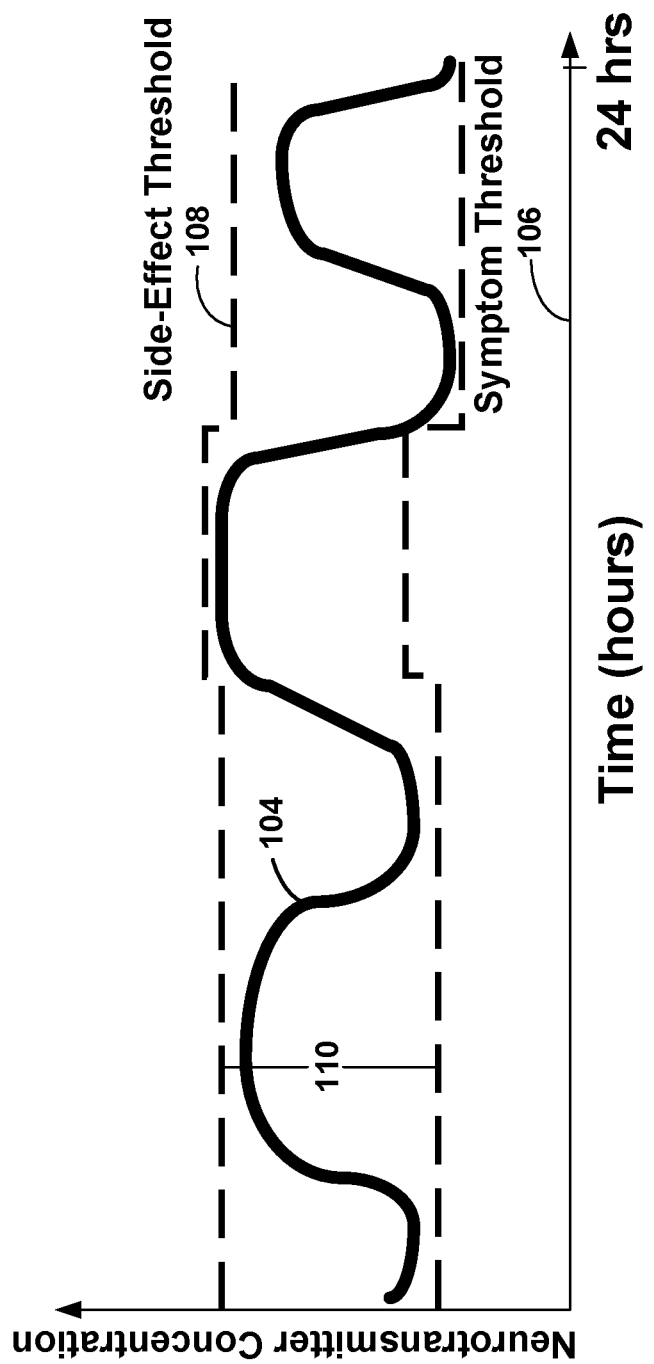

FIGS. 5A and 5B are graphs depicting examples of relative concentrations 104 of a neurotransmitter in the brain of a patient over time. FIG. 5A depicts a varying neurotransmitter level 104 as a function of time, represented over the course of a 24-hour period. As shown in FIG. 5A, neurotransmitter level 104 includes three periodic increases and corresponding subsequent decreases in neurotransmitter levels over the course of the day. These pairs of increases and decreases may represent, for example, a change in neurotransmitter levels in response to a medication consumed by the patient, among other contributing variables. As shown in FIG. 5A, the medication may be prescribed by a physician in an amount configured to maintain the varying neurotransmitter level 104 within a preferred range of neurotransmitter levels 110.

In some examples, the preferred neurotransmitter range 110 may be defined by a lower "symptom" threshold 106 and an upper "side-effect" threshold 108. For example, if neurotransmitter levels 104 fall below the symptom threshold 106, one or more symptoms of a neurological disorder, such as tremors, may begin to manifest or worsen, and stimulation therapy levels should be increased in order to assuage the symptoms. Conversely, if neurotransmitter levels 104 rise above side-effect threshold 108, the combination of elevated neurotransmitter levels and an elevated stimulation therapy level may trigger undesired side effects for the patient. As shown in FIG. 5A, neither the symptom threshold 106 nor the side-effect threshold 108 are necessarily fixed, constant, or predetermined. Any of a number of factors may affect these levels, including, as non-limiting examples, degeneration of medication over time, or an amount of food that the patient has eaten along with the oral medication that may modify the patient's tolerance for the effects of the medication.

In some examples, a particular set or range of stimulation therapy waveforms and/or waveform parameters may be determined for a patient, based on these upper and lower thresholds, during preliminary clinical evaluations with a clinician. For example, a patient may undergo preliminary testing and research to determine a customized set of waveform parameters. As one example of this preliminary process, a clinician, using therapy system 10 or another system, may perform cyclic voltammetry while the patient is off-medication and off-stimulation during a desired behavioral state (e.g. resting, engaging in entertainment, or any other behavioral task influencing the release of a neurotransmitter of interest) to determine a lower neurotransmitter concentration threshold. Then, with the patient on a therapeutic dose of medication, the clinician may determine a level of stimulation therapy where side-effects first occur, such as by using voltammetry to determine this upper concentration threshold. Based on the upper and lower thresholds, the clinician may determine a stimulation therapy setpoint or operating range. In other examples, therapy system 10 may automatically learn or determine these upper and lower thresholds from patient data inputs (e.g. a patient's self-assessment notes or records) or other sensor data (local field potential, inertial data, etc.).

In accordance with the techniques of this disclosure, FIG. 5B illustrates an example technique for modifying (e.g., determining and delivering) a level (e.g., amplitude of voltage, frequency, etc.) of stimulation therapy 112 based on measured neurotransmitter levels 104. Therapy system 10 of FIG. 1 is configured to perform cyclic voltammetry via electrodes 24, 26 to measure the level of a neurotransmitter 104 present within the brain of a patient, e.g., blood concentrations of dopamine within the patient's brain. In response to the measured neurotransmitter level, therapy system 10 is configured to select and deliver a corresponding level of stimulation therapy 112.

In one example, as shown in FIG. 5B, in response to determining a reduced neurotransmitter level 104, system 10 may select and deliver stimulation therapy 112 that has a relatively high stimulation intensity. Conversely, in response to determining a relatively high measured levels of neurotransmitter 104, system 10 may select and deliver stimulation therapy 112 that has a relatively low stimulation intensity. Accordingly, therapy system 10 may "step up" and "step down" therapy levels 112 by adjusting one or more therapy parameters by discrete units or amounts in response to relatively higher or lower measured neurotransmitter levels, respectively. The "height" and "width" of these steps (e.g., amplitude and frequency of change in therapy intensity) may be a predetermined amount, an amount programmable by a clinician, or may be determined by a model-based system, such as a proportional-integral-derivative (PID) controller or a plant model of absorption/decay of medication.

In addition to further reducing undesired symptoms and/or side effects for patient 12, the techniques of this disclosure further enable conservation of energy by reducing electrical stimulation therapy levels while medication-induced neurotransmitter levels are sufficiently high to reduce or eliminate patient symptoms without the stimulation therapy supplement.

In another example, therapy system 10 may perform cyclic voltammetry to monitor a change in neurotransmitter levels 104, for example, an increase or decrease in relative blood-dopamine concentration from a previous measurement (e.g., as stored as neurotransmitter info 76 in memory of 62 of IMD 16 of FIG. 2). Upon identifying an increase in neurotransmitter level 104 since a previous measurement, therapy delivery system 10 may decrease stimulation therapy levels 112 by an amount proportional to the increase in neurotransmitter level 104. Conversely, upon identifying a decrease in neurotransmitter level 104 since a previous measurement, therapy delivery system 10 may increase stimulation therapy levels 112 by an amount proportional to the decrease in neurotransmitter level 104. For example, memory 62 (FIG. 2) may store a table of values correlating measured changes in neurotransmitter levels to respective predetermined stimulation therapy intensities and/or changes in stimulation therapy intensities (e.g., therapy parameter(s)). In response to determining a particular change in neurotransmitter levels, processor 60 may retrieve a corresponding therapy intensity or change in therapy intensity from memory 62, and cause stimulation generator 64 to provide therapy at the determined intensity level. In some examples, therapy delivery system 10 may only modify therapy intensity levels in response to measuring a change in neurotransmitter levels that is above or below a predetermined threshold amount of change.

In some examples, therapy system 10 may be configured to adaptively switch between different waveforms, or between different pulse types (e.g., pulse shape, pulse width, etc.) within a single waveform, based on changes in other parameters. As one illustrative example, therapy system 10 may encounter a scenario in which a determined frequency of stimulation changes would otherwise result in electrical pulses that are too short in duration in a rising phase or falling phase, or would result in consecutive pulses that are too close together. In some such cases, therapy system 10 may be configured to determine that these determined changes are incompatible, e.g., that at least one pulse violates one or more predetermined limits on pulse frequency or pulse-phase duration (e.g., a duration of one phase of a biphasic pulse). Such predetermined limits may indicate, for example, that a pulse frequency or duration is greater than a maximum threshold, below a predetermined minimum threshold, or outside a range having a minimum and maximum value. In such cases, therapy system 10 may be configured to replace the offending pulse(s) with new electrical pulses having a different type (e.g., shape) in order to resolve the incompatibilities.

Figure 6:
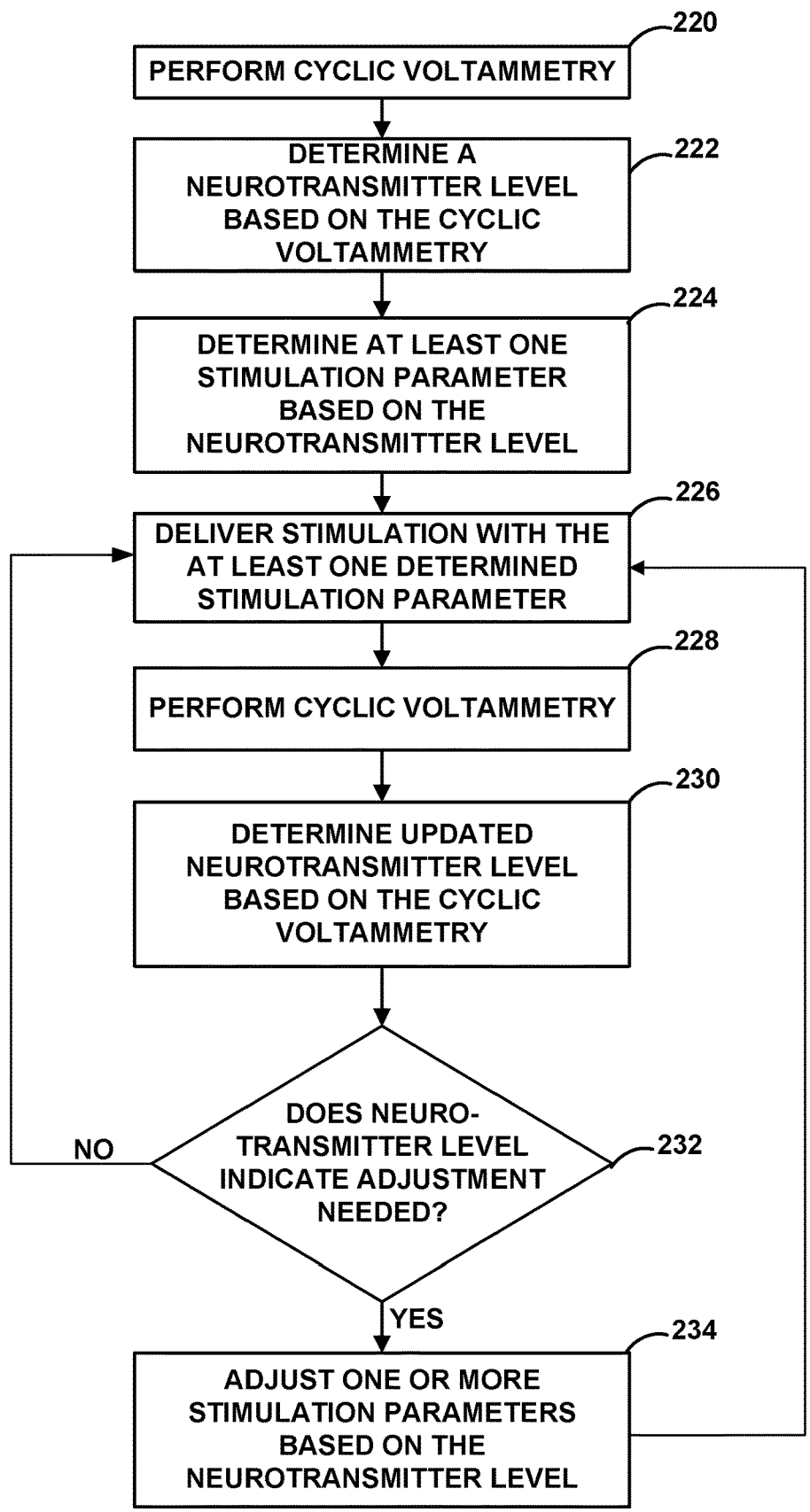
FIG. 6 is a flowchart illustrating an example method in accordance with some examples of this disclosure.

FIG. 6 is a flow diagram illustrating an example technique, consistent with the present disclosure, directed to delivering electrical stimulation therapy based on measured neurotransmitter levels, thereby improving, achieving, or maintaining a patient condition, for example, by reducing or preventing the symptoms of a patient disorder and/or the side effects of treatments associated with the patient disorder. The techniques of FIG. 6 are described with respect to therapy system 10 of FIGS. 1-3 for ease of description. Such an example technique may be employed by any system for performing such an example technique.

Sensing module 66 of IMD 16, via two or more of electrodes 24, 26 (e.g., platinum-iridium electrodes), performs cyclic voltammetry in order to measure a relative level or concentration of a neurotransmitter within the brain 28 of a patient 12 (220). For example, sensing module 66 may systematically increase and then decrease a voltage applied across a reference electrode 24, 26 implanted in the brain 28 of the patient 12, while measuring the corresponding amplitude of the electrical current induced at the reference electrode.

IMD 16 determines a neurotransmitter level based on the cyclic voltammetry measurements (222). For example, the dimensions of a cyclic voltammogram trace plotting the measured current against the applied voltage may be correlated with, or otherwise indicative of, a level or concentration of a neurotransmitter level (e.g., dopamine, serotonin, etc.) within the brain 28 of the patient 12. Processor 60 of IMD 16 may retrieve the correlation relations between voltammogram measurements and neurotransmitter levels from memory 62, and apply them to the voltammogram trace to determine a current neurotransmitter level. In some examples, but not all examples, programmer 14 may be configured to output an indication of the determined neurotransmitter levels via user interface 86, such as a display screen. For example, current neurotransmitter levels may be determined and output in units of nanomoles per liter (nmol/L) up to micromole/L.

Based on the determined neurotransmitter level, IMD 16 may determine a corresponding stimulation therapy level, including a value for at least one stimulation parameter (224). For example, IMD 16 may determine values for one or more of a set of stimulation parameters including, but not limited to, an electrical pulse width or shape, an electrical current amplitude, a voltage amplitude, a frequency, and/or a stimulation electrode combination for delivering the stimulation therapy. In some examples, IMD 16 may retrieve from memory a stimulation therapy intensity level (e.g., a specific set or range of values for stimulation parameters) corresponding to individual neurotransmitter levels or discrete ranges of neurotransmitter levels.

As one example, IMD 16 may determine a neurotransmitter level that is near or above a predetermined upper threshold. The predetermined upper threshold may indicate, for example, a neurotransmitter level indicative of a corresponding elevated medication level that may be likely to negatively interact with stimulation therapy to produce undesired side effects for the patient. In such cases, IMD 16 may determine (e.g., select) a relatively low stimulation therapy level, e.g., a relatively low electrical voltage amplitude, electrical current amplitude, etc.

In another example, IMD 16 may determine a neurotransmitter level that is near or below a predetermined lower threshold, which may indicate an increased likelihood of the onset of one or more symptoms of a disorder of patient 12. In such cases, IMD 16 may determine a relatively high stimulation therapy level, e.g., a relatively high electrical voltage amplitude, electrical current amplitude, etc.

In some examples, additionally or alternatively to determining a neurotransmitter level and determining a corresponding stimulation therapy level, IMD 16 may determine a relative change in a neurotransmitter level since a previous measurement, as stored in and retrieved from memory. In some such examples, IMD 16 may determine a corresponding change in stimulation therapy level based on (e.g., inversely proportional to) the amount of relative change in the neurotransmitter level.

After determining the corresponding stimulation therapy level or change in stimulation therapy level, stimulation generator 64 may generate and deliver, via one or more of electrodes 24, 26, stimulation therapy to patient 12 according to the determined level (226). In some examples, IMD 16 may deliver the stimulation therapy via the same, or a common subset of, electrodes 24, 26 that IMD 16 previously used to measure the neurotransmitter levels. In some examples, but not all examples, IMD 16 is configured to output for display, such as via UI 86 of patient programmer 14, an indication of the selected and/or delivered therapy, such as an indication of the delivered therapy levels. In some examples, the indication of the determined therapy level may accompany a prompt for the user (e.g., the patient or clinician) to approve or reject the indicated level. In another example, the indicated level may accompany a prompt for the patient to consume more medication, or to otherwise titrate their medication intake.

At a predetermined point in time (e.g., any amount of time, such as between tens of milliseconds and hours) subsequent to delivering the stimulation therapy (226), IMD 16 may perform, via two or more of electrodes 24, 26, subsequent cyclic voltammetry (228) in order to determine and store subsequent (e.g., "updated") neurotransmitter levels (230), as the neurotransmitter levels fluctuate over time, such as due to patient consumption of medication or other factors. In some examples herein, IMD 16 enables long-term monitoring of patient neurotransmitter levels, which a clinician may use, for example, to inform future medication prescriptions for the patient, both in type and amount.

Based on the updated neurotransmitter levels, IMD 16 may determine whether to adjust (e.g., update) the previously determined stimulation therapy levels (232). For example, IMD 16 may determine that updated stimulation therapy levels are necessary ("YES" branch of 232) in response to determining, for example, an above-threshold neurotransmitter level, a below-threshold neurotransmitter level, or a an above-threshold change in neurotransmitter level compared to the previous neurotransmitter-level measurement (e.g., an above-threshold change over time). In some such examples, IMD 16 may determine updated stimulation therapy levels (234), which may include modifying the values of one or more stimulation parameters (e.g., amplitude of voltage or current, etc.) from their previous values in response to determining a change in the neurotransmitter level from the previous measurement. As one example, IMD 16 may determine an increased neurotransmitter level, and in response, may determine (e.g., retrieve from memory) a corresponding stimulation therapy level (e.g., a value for at least one stimulation parameter) that is decreased by an amount proportional to the increase in the neurotransmitter level. As another example, IMD 16 may determine a decreased neurotransmitter level, and in response, may determine (e.g., retrieve from memory) a corresponding stimulation therapy level (e.g., a value for at least one stimulation parameter) that is increased by an amount proportional to the decrease in the neurotransmitter level. As another example, IMD 16 may determine no change or a negligible change in the neurotransmitter level, and in response, may determine (e.g., maintain) a consistent stimulation therapy level.

In some examples, such as in response to determining a particularly high neurotransmitter level (e.g., a level above a predetermined threshold), IMD 16 may determine a corresponding stimulation therapy level of zero, or in other words, IMD 16 may determine that stimulation therapy should be suspended until neurotransmitter levels decrease in order to avoid or reduce undesired side effects from the interaction between stimulation therapy and patient medication.

In response to determining one or more updated (e.g., adjusted or modified) therapy parameters (234), IMD 16 may deliver subsequent stimulation therapy according to the updated stimulation parameters (226). In other examples, IMD 16 may determine that neurotransmitter levels remain between desired upper and lower thresholds, or have not changed by an above threshold amount ("NO" branch of 232). In some such examples, IMD 16 may deliver subsequent stimulation therapy according to the previously determined therapy levels (226). In this way, IMD 16 moderates a closed feedback loop of measuring neurotransmitter levels and providing stimulation therapy based on the measured neurotransmitter levels. In other words, IMD 16 is configured to intelligently and dynamically modify stimulation therapy intensity over time, such as to complement or balance medication therapy. In some examples, IMD 16 may manifest this closed feedback loop by generating a continuous waveform (e.g., waveforms 90A-90E of FIGS. 4A-4E) that includes an alternating pattern of first electrical pulses configured to deliver stimulation therapy, and second electrical pulses configured to facilitate cyclic voltammetry measurements. In some examples, the first electrical pulses and the second electrical pulses may be interleaved with each other, or may be partially or fully integrated into each other.

In some examples, but not all examples, one or more of the steps of the techniques of FIG. 6 may be spatially divided among different locations within the brain 28 of patient 12, such as among the two hemispheres of the patient's brain. For example, in some cases a first electrode combination (e.g., a first lead) may be implanted in the left hemisphere of the brain 28, and a second electrode combination (e.g., a second lead) may be implanted in the right hemisphere of the brain 28. In some such examples, the techniques of FIG. 6 may include performing cyclic voltammetry by delivering a first electrical stimulus via the first electrode combination implanted in the left hemisphere of the brain 28 of the patient 12, and delivering a second electrical stimulus via the second electrode combination implanted in the right hemisphere of the brain 28 of the patient 12, and then monitoring a first electrical current of the first electrical stimulus and a second electrical current of the second electrical stimulus (220).

IMD 16 may then determine, based on the first electrical current, a first value representative of a first concentration of dopamine in the left hemisphere of the brain of the patient, and determine, based on the second electrical current, a second value representative of a second concentration of dopamine in the right hemisphere of the brain of the patient (222). Such examples of distinct, dual-region measurements may enable comparisons of different dopamine concentrations in different regions of the brain, which in some cases, may enable long-term monitoring of the progression of a disease or condition within the brain of the patient.

IMD 16 may then determine, based on the first value representative of the concentration of dopamine in the left hemisphere and the second value representative of the concentration of dopamine in the right hemisphere, a value for one or more stimulation parameters that at least partially define electrical stimulation therapy (226), and then deliver, via electrodes 24, 26, stimulation therapy according to the one or more stimulation parameters (228). In some examples, IMD 16 is configured to utilize additional electrodes along probes 20A, 20B to determine broader tissue response to stimulation therapy and presence of neurotransmitter concentrations.

In other examples, additionally or alternatively to conducting a first neurotransmitter measurement via a first lead implanted in a first location in the brain of a patient and conducting a second neurotransmitter measurement via a second lead implanted within a second location in the brain of the patient, in some examples, IMD 16 is configured to conduct a single cyclic-voltammetry neurotransmitter measurement via a first electrode on a first lead (e.g., implanted in one hemisphere of the brain) and a second electrode on a second lead (e.g., implanted in the other hemisphere of the brain). Such inter-lead measurements may enable a more global perspective (e.g., an average measurement) of neurotransmitter levels across the brain of the patient, as compared to more discrete, localized measurements which may vary significantly from region to region.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

The following clauses provide some examples of the disclosure.

Clause 1: In some examples, a method includes delivering, via an electrode implanted in a brain of a patient and stimulation circuitry, an electrical stimulus; monitoring an electrical current generated by the stimulation circuitry to deliver the electrical stimulus; determining, based on the electrical current, a value representative of a concentration of dopamine in the brain of the patient; determining, based on the value representative of the concentration of dopamine, a value for one or more stimulation parameters that at least partially define electrical stimulation therapy; and delivering, via the electrode, the electrical stimulation therapy. In some examples of the method of clause 1, delivering the electrical stimulus includes delivering the electrical stimulus via a first electrode combination that includes the electrode, and delivering stimulation therapy includes delivering stimulation therapy via a second electrode combination that includes the electrode, wherein the first electrode combination is different from the second combination.

In other examples of the method of clause 1: the electrode is a first electrode, delivering the electrical stimulus includes delivering the electrical stimulus via a first electrode combination including the first electrode and a second electrode, delivering the electrical stimulation therapy includes delivering the electrical stimulation therapy via a second electrode combination comprising the first electrode and the second electrode, and the first electrode combination is the same as the second electrode combination.

Clause 2: In some examples of the method of clause 1, the electrode includes at least one platinum-iridium electrode.

Clause 3: In some examples of the method of clause 1 or clause 2, the electrical stimulus includes a first electrical stimulus, the electrical current includes a first electrical current, the value includes a first value, and the concentration includes a first concentration, and the method further includes: delivering, via the electrode implanted in the brain of the patient and the stimulation circuitry, a second electrical stimulus; monitoring a second electrical current generated by the stimulation circuitry to deliver the second electrical stimulus; and determining, based on the second electrical current, a second value representative of a second concentration of dopamine in the brain of the patient.

Clause 4: In some examples of the method of clause 3, the electrical stimulation therapy includes a first electrical stimulation therapy, determining the second value representative of the second concentration of dopamine in the brain of the patient includes determining that the second concentration of dopamine exceeds a threshold concentration, and the method further includes delivering, via the electrode, a second electrical stimulation therapy, wherein a second voltage of the second electrical stimulation therapy is less than a first voltage of the first electrical stimulation therapy.

Clause 5: In some examples of the method of clause 3, the electrical stimulation therapy includes a first electrical stimulation therapy, determining the second value representative of the second concentration of dopamine in the brain of the patient includes determining that the second concentration of dopamine is below a threshold concentration, and the method further includes delivering, via the electrode, a second electrical stimulation therapy, wherein a second voltage of the second electrical stimulation therapy is greater than a first voltage of the first electrical stimulation therapy.

Clause 6: In some examples of the method of any of clauses 1-5, delivering the electrical stimulus and delivering the electrical stimulation therapy includes providing, via the electrode, interleaving electrical stimulus pulses and electrical stimulation therapy pulses.

Clause 7: In some examples of the method of any of clauses 1-6, delivering the electrical stimulus and delivering the electrical stimulation therapy includes delivering, via the electrode, the electrical stimulus and the electrical stimulation therapy within a common electrical pulse.

Clause 8: In some examples of the method of clause 7, the common electrical pulse includes a square wave, and delivering the electrical stimulus and delivering the electrical stimulation therapy further includes: increasing a pulse voltage of the common pulse from a minimum voltage to a therapy-level voltage while monitoring the electrical current; maintaining the pulse voltage at the therapy-level voltage for a predetermined duration; and reducing the pulse voltage from the therapy-level voltage to the minimum voltage.

Clause 9: In some examples of the method of clause 7, the common electrical pulse includes a triangle wave, and delivering the electrical stimulus and delivering the electrical stimulation therapy further includes: increasing a pulse voltage of the common pulse from a minimum voltage to a therapy-level voltage while monitoring the electrical current; and reducing the pulse voltage from the therapy-level voltage to the minimum voltage.

Clause 10: In some examples of the method of any of clauses 1-9, the method further includes outputting, for display, the value representative of the concentration of dopamine in the brain of the patient.

Clause 11: In some examples of the method of clause 10, the method further includes outputting, for display, therapy information including a time of therapy delivery or stimulation parameter values corresponding to dopamine measurements.

Clause 12: In some examples of the method of any of clauses 1-11, delivering the electrical stimulus includes delivering a first electrical stimulus generated by stimulation circuitry via a first electrode implanted in a left hemisphere of the brain of the patient and delivering a second electrical stimulus generated by the stimulation circuitry via a second electrode implanted in a right hemisphere of the brain of the patient, and the method further includes: monitoring a first electrical current generated by the stimulation circuitry to deliver the first electrical stimulus and a second electrical current generated by the stimulation circuitry to deliver the second electrical stimulus; determining, based on the first electrical current, a first value representative of a concentration of dopamine in the left hemisphere of the brain of the patient; determining, based on the second electrical current, a second value representative of a concentration of dopamine in the right hemisphere of the brain of the patient; and determining, based on the first value representative of the concentration of dopamine in the left hemisphere and the second value representative of the concentration of dopamine in the right hemisphere, a value for one or more stimulation parameters that at least partially define electrical stimulation therapy.

Clause 13: In some examples of the method of any of clauses 1-12, the one or more stimulation parameters include one or more first stimulation parameters defining a first waveform comprising first electrical pulses each comprising a first pulse shape, and the method further includes: determining that at least one of the first electrical pulses violates a predetermined limit on pulse frequency or pulse-phase duration; determining, in response to the determination that at least one of the first electrical pulses violates the predetermined limit on the pulse frequency or the pulse-phase duration, a second waveform comprising second electrical pulses each comprising a second pulse shape, wherein the second pulse shape is different from the first pulse shape; and delivering, via the electrode, the electrical stimulation therapy, wherein the electrical stimulation therapy is at least partially defined by the second waveform.

Clause 14: In some examples, a system includes: an electrode configured to be implanted in a brain of a patient; stimulation circuitry; and processing circuitry configured to: cause the stimulation circuitry to deliver, via the electrode implanted in the brain of the patient, an electrical stimulus; monitor an electrical current generated by the stimulation circuitry to deliver the electrical stimulus; determine, based on the electrical current, a value representative of a concentration of dopamine in the brain of the patient; determine, based on the value representative of the concentration of dopamine, a value for one or more stimulation parameters that at least partially define electrical stimulation therapy; and cause the stimulation circuitry to deliver, via the electrode, the electrical stimulation therapy. In some examples of the system of clause 14, delivering the electrical stimulus includes delivering the electrical stimulus via a first electrode combination that includes the electrode, and delivering stimulation therapy includes delivering stimulation therapy via a second electrode combination that includes the electrode, wherein the first electrode combination is different from the second combination.

In other examples of the system of clause 14: the electrode is a first electrode, delivering the electrical stimulus includes delivering the electrical stimulus via a first electrode combination including the first electrode and a second electrode, delivering the electrical stimulation therapy includes delivering the electrical stimulation therapy via a second electrode combination comprising the first electrode and the second electrode, and the first electrode combination is the same as the second electrode combination.

Clause 15: In some examples of the system of clause 14, the electrode includes at least one platinum-iridium electrode.

Clause 16: In some examples of the system of clause 14 or clause 15, the electrical stimulus includes a first electrical stimulus, the electrical current includes a first electrical current, the value includes a first value, the concentration includes a first concentration, and the method further includes: causing the stimulation circuity to deliver, via the electrode implanted in the brain of the patient, a second electrical stimulus; monitoring a second electrical current generated by the stimulation circuitry to deliver the second electrical stimulus; and determining, based on the second electrical current, a second value representative of a second concentration of dopamine in the brain of the patient.

Clause 17: In some examples of the system of clause 14 or clause 15, the electrical stimulation therapy includes a first electrical stimulation therapy, determining the second value representative of the second concentration of dopamine in the brain of the patient includes determining that the second concentration of dopamine exceeds a threshold concentration, and the method further includes delivering, via the electrode, a second electrical stimulation therapy, wherein a second voltage of the second electrical stimulation therapy is less than a first voltage of the first electrical stimulation therapy.

Clause 18: In some examples of the system of any of clauses 14-17, the electrical stimulation therapy includes a first electrical stimulation therapy, determining the second value representative of the second concentration of dopamine in the brain of the patient includes determining that the second concentration of dopamine is below a threshold concentration, and the method further includes delivering, via the electrode, a second electrical stimulation therapy, wherein a second voltage of the second electrical stimulation therapy is greater than a first voltage of the first electrical stimulation therapy.

Clause 19: In some examples of the system of any of clauses 14-18, delivering the electrical stimulus and delivering the electrical stimulation therapy includes providing, via the electrode, interleaving electrical stimulus pulses and electrical stimulation therapy pulses.

Clause 20: In some examples of the system of any of clauses 14-19, delivering the electrical stimulus and delivering the electrical stimulation therapy includes delivering, via the electrode, the electrical stimulus and the electrical stimulation therapy within a common electrical pulse.

Clause 21: In some examples of the system of clause 20, the common electrical pulse includes a square wave, delivering the electrical stimulus and delivering the electrical stimulation therapy further includes: increasing a pulse voltage of the common pulse from a minimum voltage to a therapy-level voltage while monitoring the electrical current; maintaining the pulse voltage at the therapy-level voltage for a predetermined duration; and reducing the pulse voltage from the therapy-level voltage to the minimum voltage.

Clause 22: In some examples of the system of clause 20, the common electrical pulse includes a triangle wave, and delivering the electrical stimulus and delivering the electrical stimulation therapy further includes: increasing a pulse voltage of the common pulse from a minimum voltage to a therapy-level voltage while monitoring the electrical current; and reducing the pulse voltage from the therapy-level voltage to the minimum voltage.

Clause 23: In some examples of the system of any of clauses 14-22, the processing circuitry is further configured to output, for display, the value representative of the concentration of dopamine in the brain of the patient.

Clause 24: In some examples of the system of any of clauses 14-23, the processing circuitry is further configured to output, for display, therapy information including a time of therapy delivery or stimulation parameter values corresponding to dopamine measurements.

Clause 25: In some examples of the system of any of clauses 14-24, delivering the electrical stimulus includes delivering a first electrical stimulus generated by stimulation circuitry via a first electrode implanted in a left hemisphere of the brain of the patient and delivering a second electrical stimulus generated by the stimulation circuitry via a second electrode implanted in a right hemisphere of the brain of the patient, and the method further includes: monitoring a first electrical current generated by the stimulation circuitry to deliver the first electrical stimulus and a second electrical current generated by the stimulation circuitry to deliver the second electrical stimulus; determining, based on the first electrical current, a first value representative of a concentration of dopamine in the left hemisphere of the brain of the patient; determining, based on the second electrical current, a second value representative of a concentration of dopamine in the right hemisphere of the brain of the patient; and determining, based on the first value representative of the concentration of dopamine in the left hemisphere and the second value representative of the concentration of dopamine in the right hemisphere, a value for one or more stimulation parameters that at least partially define electrical stimulation therapy.

Clause 26: In some examples of the system of any of clauses 14-25, the system further includes an implantable medical device including the electrode and the stimulation circuitry.

Clause 27: In some examples, a computer-readable storage medium includes instructions that when executed by a processor, cause the processor to: deliver, via an electrode implanted in a brain of a patient and stimulation circuitry, an electrical stimulus; monitor an electrical current generated by the stimulation circuitry to deliver the electrical stimulus; determine, based on the electrical current, a value representative of a concentration of dopamine in the brain of the patient; determine, based on the value representative of the concentration of dopamine, a value for one or more stimulation parameters that at least partially define electrical stimulation therapy; and deliver, via the electrode, the electrical stimulation therapy. In some examples of the computer-readable storage medium of clause 27, delivering the electrical stimulus includes delivering the electrical stimulus via a first electrode combination that includes the electrode, and delivering stimulation therapy includes delivering stimulation therapy via a second electrode combination that includes the electrode, wherein the first electrode combination is different from the second combination.

In other examples of the computer-readable storage medium of clause 27: the electrode is a first electrode, delivering the electrical stimulus includes delivering the electrical stimulus via a first electrode combination including the first electrode and a second electrode, delivering the electrical stimulation therapy includes delivering the electrical stimulation therapy via a second electrode combination comprising the first electrode and the second electrode, and the first electrode combination is the same as the second electrode combination.

Clause 28: In some examples of the computer-readable storage medium of clause 26, the electrode includes at least one platinum-iridium electrode.

Clause 29: In some examples of the computer-readable storage medium of clause 27 or clause 28, the electrical stimulus includes a first electrical stimulus, the electrical current includes a first electrical current, the value includes a first value, and the concentration includes a first concentration, and the instructions further cause the processing circuitry to: deliver, via the electrode implanted in the brain of the patient the and stimulation circuitry, a second electrical stimulus; monitor a second electrical current generated by the stimulation circuitry to deliver the second electrical stimulus; and determine, based on the second electrical current, a second value representative of a second concentration of dopamine in the brain of the patient.

Clause 30: In some examples of the computer-readable storage medium of any of clauses 27-29, the electrical stimulation therapy includes a first electrical stimulation therapy, and the instructions further cause the processor to deliver, via the electrode, a second electrical stimulation therapy, wherein a second voltage of the second electrical stimulation therapy is less than a first voltage of the first electrical stimulation therapy.

Clause 31: In some examples of the computer-readable storage medium of any of clauses 27-29, the electrical stimulation therapy includes a first electrical stimulation therapy, and the instructions further cause the processor to deliver, via the electrode, a second electrical stimulation therapy, wherein a second voltage of the second electrical stimulation therapy is greater than a first voltage of the first electrical stimulation therapy.

Clause 32: In some examples of the computer-readable storage medium of any of clauses 27-31, the instructions configure the processor to deliver, via the electrode, interleaving electrical stimulus pulses and electrical stimulation therapy pulses.

Clause 33: In some examples of the computer-readable storage medium of any of clauses 27-32, the instructions configure the processor to deliver, via the electrode, the electrical stimulus and the electrical stimulation therapy within a common electrical pulse.

Clause 34: In some examples of the computer-readable storage medium of clause 33, the common electrical pulse includes a square wave, and the instructions further cause the processor to: increase a pulse voltage of the common pulse from a minimum voltage to a therapy-level voltage while monitoring the electrical current; maintain the pulse voltage at the therapy-level voltage for a predetermined duration; and reduce the pulse voltage from the therapy-level voltage to the minimum voltage.

Clause 35: In some examples of the computer-readable storage medium of clause 33, the common electrical pulse includes a triangle wave, and the instructions further cause the processor to: increase a pulse voltage of the common pulse from a minimum voltage to a therapy-level voltage while monitoring the electrical current; and reduce the pulse voltage from the therapy-level voltage to the minimum voltage.

Clause 36: In some examples of the computer-readable storage medium of any of clauses 27-35, the instructions further cause the processor to output for display the value representative of the concentration of dopamine in the brain of the patient.

Clause 37: In some examples of the computer-readable storage medium of clause 36, the instructions further cause the processor to output for display therapy information including a time of therapy delivery or stimulation parameter values corresponding to dopamine measurements.

Clause 38: In some examples of the computer-readable storage medium of any of clauses 27-37, the instructions further cause the processor to: monitor a first electrical current generated by the stimulation circuitry to deliver the first electrical stimulus and a second electrical current generated by the stimulation circuitry to deliver the second electrical stimulus; determine, based on the first electrical current, a first value representative of a concentration of dopamine in the left hemisphere of the brain of the patient; determine, based on the second electrical current, a second value representative of a concentration of dopamine in the right hemisphere of the brain of the patient; and determine, based on the first value representative of the concentration of dopamine in the left hemisphere and the second value representative of the concentration of dopamine in the right hemisphere, a value for one or more stimulation parameters that at least partially define electrical stimulation therapy.

Various examples of the disclosure have been described. These and other examples are within the scope of the following claims.

What is claimed is:

1. A method comprising:
   delivering, via an electrode implanted in a brain of a patient and stimulation circuitry, electrical stimulation therapy comprising an electrical stimulus;
   monitoring an electrical current generated by the stimulation circuitry to deliver the electrical stimulus;
   determining, based on the electrical current, a value representative of a concentration of dopamine in the brain of the patient;
   determining, based on the value representative of the concentration of dopamine, a value for one or more stimulation parameters that at least partially define subsequent electrical stimuli of the electrical stimulation therapy; and
   delivering, via the electrode, the subsequent electrical stimuli of the electrical stimulation therapy according to the value of the one or more stimulation parameters.

2. The method of claim 1, wherein
   delivering the electrical stimulus comprises delivering the electrical stimulus via an electrode combination that includes the electrode.

3. The method of claim 1, wherein the electrode is a first electrode, and wherein:

delivering the electrical stimulus comprises delivering the electrical stimulus via a first electrode combination comprising the first electrode and a second electrode, delivering the electrical stimulation therapy comprises delivering the electrical stimulation therapy via a second electrode combination comprising the first electrode and the second electrode, and the first electrode combination is the same as the second electrode combination.

4. The method of claim 1, wherein the electrode comprises a platinum-iridium electrode.

5. The method of claim 1, wherein the electrical stimulus comprises a first electrical stimulus, the electrical current comprises a first electrical current, the value comprises a first value, and the concentration comprises a first concentration, and wherein the method further comprises:

delivering, via the electrode implanted in the brain of the patient and the stimulation circuitry, a second electrical stimulus;

monitoring a second electrical current generated by the stimulation circuitry to deliver the second electrical stimulus; and determining, based on the second electrical current, a second value representative of a second concentration of dopamine in the brain of the patient.

6. The method of claim 5, wherein the electrical stimulation therapy comprises a first electrical stimulation therapy, wherein determining the second value representative of the second concentration of dopamine in the brain of the patient comprises determining that the second concentration of dopamine exceeds a threshold concentration, and wherein the method further comprises delivering, via the electrode, a second electrical stimulation therapy, wherein a second voltage of the second electrical stimulation therapy is less than a first voltage of the first electrical stimulation therapy.

7. The method of claim 5, wherein the electrical stimulation therapy comprises a first electrical stimulation therapy, wherein determining the second value representative of the second concentration of dopamine in the brain of the patient comprises determining that the second concentration of dopamine is below a threshold concentration, and wherein the method further comprises delivering, via the electrode, a second electrical stimulation therapy, wherein a second voltage of the second electrical stimulation therapy is greater than a first voltage of the first electrical stimulation therapy.

8. The method of claim 1, wherein the electrical stimulus comprises a square wave, wherein delivering the electrical stimulus and delivering the electrical stimulation therapy further comprises:

increasing a pulse voltage of the electrical stimulus from a minimum voltage to a therapy-level voltage while monitoring the electrical current;

maintaining the pulse voltage at the therapy-level voltage for a predetermined duration; and reducing the pulse voltage from the therapy-level voltage to the minimum voltage.

9. The method of claim 1, wherein the electrical stimulus comprises a triangle wave, wherein delivering the electrical stimulus and delivering the electrical stimulation therapy further comprises:

increasing a pulse voltage of the electrical stimulus from a minimum voltage to a therapy-level voltage while monitoring the electrical current; and reducing the pulse voltage from the therapy-level voltage to the minimum voltage.

10. The method of claim 1, further comprising outputting, for display, the value representative of the concentration of dopamine in the brain of the patient.

11. The method of claim 10, further comprising outputting, for display, therapy information comprising a time of therapy delivery or stimulation parameter values corresponding to dopamine measurements.

12. The method of claim 1, wherein delivering the electrical stimulus comprises delivering a first electrical stimulus generated by stimulation circuitry via a first electrode implanted in a left hemisphere of the brain of the patient and delivering a second electrical stimulus generated by the stimulation circuitry via a second electrode implanted in a right hemisphere of the brain of the patient, wherein the method further comprises:

monitoring a first electrical current generated by the stimulation circuitry to deliver the first electrical stimulus and a second electrical current generated by the stimulation circuitry to deliver the second electrical stimulus;

determining, based on the first electrical current, a first value representative of a concentration of dopamine in the left hemisphere of the brain of the patient;

determining, based on the second electrical current, a second value representative of a concentration of dopamine in the right hemisphere of the brain of the patient; and determining, based on the first value representative of the concentration of dopamine in the left hemisphere and the second value representative of the concentration of dopamine in the right hemisphere, a value for the one or more stimulation parameters that at least partially define the subsequent electrical stimuli of the electrical stimulation therapy.

13. The method of claim 1, wherein the one or more stimulation parameters comprise one or more first stimulation parameters defining a first waveform comprising first electrical pulses each comprising a first pulse shape, and wherein the method further comprises:

determining that at least one of the first electrical pulses violates a predetermined limit on pulse frequency or pulse-phase duration;

determining, in response to the determination that at least one of the first electrical pulses violates the predetermined limit on the pulse frequency or the pulse-phase duration, a second waveform comprising second electrical pulses each comprising a second pulse shape, wherein the second pulse shape is different from the first pulse shape; and delivering, via the electrode, the electrical stimulation therapy, wherein the electrical stimulation therapy is at least partially defined by the second waveform.

14. A system comprising:

an electrode configured to be implanted in a brain of a patient;

stimulation circuitry; and processing circuitry configured to:

cause the stimulation circuitry to deliver, via the electrode implanted in the brain of the patient, electrical stimulation therapy comprising an electrical stimulus;

monitor an electrical current generated by the stimulation circuitry to deliver the electrical stimulus;

determine, based on the electrical current, a value representative of a concentration of dopamine in the brain of the patient;

determine, based on the value representative of the concentration of dopamine, a value for one or more stimulation parameters that at least partially define subsequent electrical stimuli of the electrical stimulation therapy; and cause the stimulation circuitry to deliver, via the electrode, the subsequent electrical stimuli of the electrical stimulation therapy according to the value of the one or more stimulation parameters.

15. The system of claim 14, wherein the electrical stimulus comprises a first electrical stimulus, wherein the electrical current comprises a first electrical current, wherein the value comprises a first value, and wherein the concentration comprises a first concentration, and wherein the processing circuitry is further configured to:

cause the stimulation circuitry to deliver, via the electrode implanted in the brain of the patient, a second electrical stimulus;

monitor a second electrical current generated by the stimulation circuitry to deliver the second electrical stimulus; and determine, based on the second electrical current, a second value representative of a second concentration of dopamine in the brain of the patient.

16. The system of claim 14, further comprising an implantable medical device comprising the electrode and the stimulation circuitry.

17. The system of claim 14, wherein delivering the electrical stimulus comprises delivering the electrical stimulus via an electrode combination that includes the electrode.

18. The system of claim 14, wherein the electrode is a first electrode, and wherein:

delivering the electrical stimulus comprises delivering the electrical stimulus via a first electrode combination comprising the first electrode and a second electrode, delivering the electrical stimulation therapy comprises delivering the electrical stimulation therapy via a second electrode combination comprising the first electrode and the second electrode, and the first electrode combination is the same as the second electrode combination.

19. A computer-readable storage medium comprising instructions that when executed by a processor, cause the processor to:

deliver, via an electrode implanted in a brain of a patient and stimulation circuitry, electrical stimulation therapy comprising an electrical stimulus;

monitor an electrical current generated by the stimulation circuitry to deliver the electrical stimulus;

determine, based on the electrical current, a value representative of a concentration of dopamine in the brain of the patient;

determine, based on the value representative of the concentration of dopamine, a value for one or more stimulation parameters that at least partially define subsequent electrical stimuli of the electrical stimulation therapy; and deliver, via the electrode, the subsequent electrical stimuli of the electrical stimulation therapy according to the value of the one or more stimulation parameters.

* * * * *